(12) United States Patent
Nielsen et al.

(10) Patent No.: US 9,290,758 B2
(45) Date of Patent: *Mar. 22, 2016

(54) POTENT ANTI APOB ANTISENSE COMPOUNDS

(75) Inventors: Niels Fisker Nielsen, Kgs. Lyngby (DK); Ellen Marie Straarup, Birkerod (DK); Marie Wickstrom Lindholm, Malmo (SE)

(73) Assignee: Roche Innovation Center Copenhagen A/S, Hoersholm (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/140,777

(22) PCT Filed: Jun. 14, 2010

(86) PCT No.: PCT/EP2010/058278
§ 371 (c)(1),
(2), (4) Date: Sep. 26, 2011

(87) PCT Pub. No.: WO2010/142805
PCT Pub. Date: Dec. 16, 2010

(65) Prior Publication Data
US 2012/0115936 A1    May 10, 2012

Related U.S. Application Data

(60) Provisional application No. 61/253,090, filed on Oct. 20, 2009, provisional application No. 61/186,388, filed on Jun. 12, 2009.

(30) Foreign Application Priority Data

Dec. 18, 2009  (WO) ................. PCT/EP2009/067561

(51) Int. Cl.
*C07H 1/00* (2006.01)
*C12N 15/113* (2010.01)
*A61K 31/712* (2006.01)
*A61K 31/713* (2006.01)

(52) U.S. Cl.
CPC ............ *C12N 15/113* (2013.01); *A61K 31/712* (2013.01); *A61K 31/713* (2013.01); *C12N 2310/11* (2013.01); *C12N 2310/315* (2013.01); *C12N 2310/321* (2013.01); *C12N 2310/322* (2013.01); *C12N 2310/3231* (2013.01)

(58) Field of Classification Search
None
See application file for complete search history.

(56) References Cited

U.S. PATENT DOCUMENTS

2007/0275914 A1 * 11/2007 Manoharan et al. ............ 514/44
2008/0242629 A1    10/2008 Crooke et al.

FOREIGN PATENT DOCUMENTS

| WO | WO2004/091515 | 10/2004 |
| WO | WO 2004/091515 | * 10/2004 |
| WO | WO2006/053430 | 5/2006 |
| WO | WO2007/031081 | 3/2007 |
| WO | WO2007/107162 | 9/2007 |
| WO | WO2008/113830 | 9/2008 |

OTHER PUBLICATIONS

Rosanne M. Crooke et al., "An apolipoprotein B antisense oligonucleotide lowers LDL cholesterol in hyperlipidemic mice without causing hepatic steatosis," Journal of Lipid Research, 46(5):872-884 (2005).

* cited by examiner

*Primary Examiner* — Jennifer Pitrak McDonald
(74) *Attorney, Agent, or Firm* — Fish & Richardson P.C.

(57) ABSTRACT

The present invention relates to oligomer compounds (oligomers), which target APO-B100 mRNA in a cell, leading to reduced expression of APO-B100. Reduction of APO-B100 expression is beneficial for the treatment of certain medical disorders, such as diseases associated with apolipoproteinB activity, such as in non-limiting example, different types of HDL/LDL cholesterol imbalance; dyslipidemias, e.g., familial combined dyslipidemia (FCHL), acquired hyperlipidemia, hypercholesterolemia, statin-resistant hypercholesterolemia; coronary artery disease (CAD), coronary heart disease (CHD), atherosclerosis.

18 Claims, 7 Drawing Sheets

SEQUENCE LISTING

<160> NUMBER OF SEQ ID NOS: 51

<210> SEQ ID NO 1
<211> LENGTH: 14
<212> TYPE: DNA

-continued

```
<213> ORGANISM: Artificial Sequence
<220> FEATURE:
<223> OTHER INFORMATION: Description of Artificial Sequence: Synthetic
      oligonucleotide

<400> SEQUENCE: 1
tctgaagtcc atga                                                        14

<210> SEQ ID NO 2
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ggatcaaata taag                                                        14

<210> SEQ ID NO 3
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gttgacactg tctg                                                        14

<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gttgacactg tc                                                          12

<210> SEQ ID NO 5
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gactgcctgt tctc                                                        14

<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cgttggagta agc                                                         13

<210> SEQ ID NO 7
<211> LENGTH: 14
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 7
gcgttggagt aagc                                                           14

<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ctctgtgatc cagg                                                           14

<210> SEQ ID NO 9
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ggactctgtg atcc                                                           14

<210> SEQ ID NO 10
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ctgtttgagg gact                                                           14

<210> SEQ ID NO 11
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gagatggcag atgg                                                           14

<210> SEQ ID NO 12
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gctggtgttg ccac                                                           14

<210> SEQ ID NO 13
<211> LENGTH: 13
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 13
cagatccttg cac                                                             13

<210> SEQ ID NO 14
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ccagatcctt gcac                                                            14

<210> SEQ ID NO 15
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
accttttgag ac                                                              12

<210> SEQ ID NO 16
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
caatgttcag actg                                                            14

<210> SEQ ID NO 17
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cctgcaatgt tcag                                                            14

<210> SEQ ID NO 18
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tagggctgta gctg                                                            14

<210> SEQ ID NO 19
<211> LENGTH: 14
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 19
gttggtctac ttca                                                                 14

<210> SEQ ID NO 20
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ccaaccaatt tctc                                                                 14

<210> SEQ ID NO 21
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gtcaattgta aagg                                                                 14

<210> SEQ ID NO 22
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gtttaagaaa tcca                                                                 14

<210> SEQ ID NO 23
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cttagtgtta gc                                                                   12

<210> SEQ ID NO 24
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ggttcttagt gt                                                                   12

<210> SEQ ID NO 25
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ctggttctta gtgt                                                                14

<210> SEQ ID NO 26
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(14)
<223> OTHER INFORMATION: Phosphorothioate linkage
<220> FEATURE:
<221> NAME/KEY: modified_base
<222> LOCATION: (1)..(1)
<223> OTHER INFORMATION: Oxy-LNA
<220> FEATURE:
<221> NAME/KEY: modified_base
<222> LOCATION: (2)..(2)
<223> OTHER INFORMATION: Oxy-methyl-LNA
<220> FEATURE:
<221> NAME/KEY: modified_base
<222> LOCATION: (3)..(3)
<223> OTHER INFORMATION: Oxy-LNA
<220> FEATURE:
<221> NAME/KEY: modified_base
<222> LOCATION: (12)..(14)
<223> OTHER INFORMATION: Oxy-LNA

<400> SEQUENCE: 26
tctgaagtcc atga                                                                14

<210> SEQ ID NO 27
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(14)
<223> OTHER INFORMATION: Phosphorothioate linkage
<220> FEATURE:
<221> NAME/KEY: modified_base
<222> LOCATION: (1)..(3)
<223> OTHER INFORMATION: Oxy-LNA
<220> FEATURE:
<221> NAME/KEY: modified_base
<222> LOCATION: (12)..(14)
<223> OTHER INFORMATION: Oxy-LNA

<400> SEQUENCE: 27
ggatcaaata taag                                                                14

<210> SEQ ID NO 28
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(14)
<223> OTHER INFORMATION: Phosphorothioate linkage
<220> FEATURE:
<221> NAME/KEY: modified_base
<222> LOCATION: (1)..(3)
<223> OTHER INFORMATION: Oxy-LNA

```
<220> FEATURE:
<221> NAME/KEY: modified_base
<222> LOCATION: (12)..(12)
<223> OTHER INFORMATION: Oxy-methyl-LNA
<220> FEATURE:
<221> NAME/KEY: modified_base
<222> LOCATION: (13)..(14)
<223> OTHER INFORMATION: Oxy-LNA

<400> SEQUENCE: 28
gttgacactg tctg                                                       14

<210> SEQ ID NO 29
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: modified_base
<222> LOCATION: (1)..(2)
<223> OTHER INFORMATION: Oxy-LNA
<220> FEATURE:
<221> NAME/KEY: modified_base
<222> LOCATION: (11)..(11)
<223> OTHER INFORMATION: Oxy-LNA
<220> FEATURE:
<221> NAME/KEY: modified_base
<222> LOCATION: (12)..(12)
<223> OTHER INFORMATION: Oxy-methyl-LNA

<400> SEQUENCE: 29
gttgacactg tc                                                         12

<210> SEQ ID NO 30
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(14)
<223> OTHER INFORMATION: Phosphorothioate linkage
<220> FEATURE:
<221> NAME/KEY: modified_base
<222> LOCATION: (1)..(2)
<223> OTHER INFORMATION: Oxy-LNA
<220> FEATURE:
<221> NAME/KEY: modified_base
<222> LOCATION: (3)..(3)
<223> OTHER INFORMATION: Oxy-methyl-LNA
<220> FEATURE:
<221> NAME/KEY: modified_base
<222> LOCATION: (12)..(12)
<223> OTHER INFORMATION: Oxy-methyl-LNA
<220> FEATURE:
<221> NAME/KEY: modified_base
<222> LOCATION: (13)..(13)
<223> OTHER INFORMATION: Oxy-LNA
<220> FEATURE:
<221> NAME/KEY: modified_base
<222> LOCATION: (14)..(14)
<223> OTHER INFORMATION: Oxy-methyl-LNA

<400> SEQUENCE: 30
gactgcctgt tctc                                                       14
```

```
<210> SEQ ID NO 31
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(13)
<223> OTHER INFORMATION: Phosphorothioate linkage
<220> FEATURE:
<221> NAME/KEY: modified_base
<222> LOCATION: (1)..(1)
<223> OTHER INFORMATION: Oxy-methyl-LNA
<220> FEATURE:
<221> NAME/KEY: modified_base
<222> LOCATION: (2)..(3)
<223> OTHER INFORMATION: Oxy-LNA
<220> FEATURE:
<221> NAME/KEY: modified_base
<222> LOCATION: (12)..(12)
<223> OTHER INFORMATION: Oxy-LNA
<220> FEATURE:
<221> NAME/KEY: modified_base
<222> LOCATION: (13)..(13)
<223> OTHER INFORMATION: Oxy-methyl-LNA

<400> SEQUENCE: 31
cgttggagta agc                                                          13

<210> SEQ ID NO 32
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(14)
<223> OTHER INFORMATION: Phosphorothioate linkage
<220> FEATURE:
<221> NAME/KEY: modified_base
<222> LOCATION: (1)..(1)
<223> OTHER INFORMATION: Oxy-LNA
<220> FEATURE:
<221> NAME/KEY: modified_base
<222> LOCATION: (2)..(2)
<223> OTHER INFORMATION: Oxy-methyl-LNA
<220> FEATURE:
<221> NAME/KEY: modified_base
<222> LOCATION: (3)..(3)
<223> OTHER INFORMATION: Oxy-LNA
<220> FEATURE:
<221> NAME/KEY: modified_base
<222> LOCATION: (12)..(13)
<223> OTHER INFORMATION: Oxy-LNA
<220> FEATURE:
<221> NAME/KEY: modified_base
<222> LOCATION: (14)..(14)
<223> OTHER INFORMATION: Oxy-methyl-LNA

<400> SEQUENCE: 32
gcgttggagt aagc                                                         14

<210> SEQ ID NO 33
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(1)
<223> OTHER INFORMATION: Oxy-methyl-LNA
<220> FEATURE:
<221> NAME/KEY: modified_base
<222> LOCATION: (2)..(2)
<223> OTHER INFORMATION: Oxy-LNA
<220> FEATURE:
<221> NAME/KEY: modified_base
<222> LOCATION: (3)..(3)
<223> OTHER INFORMATION: Oxy-methyl-LNA
<220> FEATURE:
<221> NAME/KEY: misc_feature
<222> LOCATION: (6)..(14)
<223> OTHER INFORMATION: Phosphorothioate linkage
<220> FEATURE:
<221> NAME/KEY: modified_base
<222> LOCATION: (12)..(14)
<223> OTHER INFORMATION: Oxy-LNA

<400> SEQUENCE: 33
ctctgtgatc cagg                                                   14

<210> SEQ ID NO 34
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(14)
<223> OTHER INFORMATION: Phosphorothioate linkage
<220> FEATURE:
<221> NAME/KEY: modified_base
<222> LOCATION: (1)..(3)
<223> OTHER INFORMATION: Oxy-LNA
<220> FEATURE:
<221> NAME/KEY: modified_base
<222> LOCATION: (12)..(12)
<223> OTHER INFORMATION: Oxy-LNA
<220> FEATURE:
<221> NAME/KEY: modified_base
<222> LOCATION: (13)..(14)
<223> OTHER INFORMATION: Oxy-methyl-LNA

<400> SEQUENCE: 34
ggactctgtg atcc                                                   14

<210> SEQ ID NO 35
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(14)
<223> OTHER INFORMATION: Phosphorothioate linkage
<220> FEATURE:
<221> NAME/KEY: modified_base
<222> LOCATION: (1)..(1)
<223> OTHER INFORMATION: Oxy-methyl-LNA
<220> FEATURE:
<221> NAME/KEY: modified_base
<222> LOCATION: (2)..(3)
<223> OTHER INFORMATION: Oxy-LNA
<220> FEATURE:
<221> NAME/KEY: modified_base
```

```
<222> LOCATION: (12)..(12)
<223> OTHER INFORMATION: Oxy-LNA
<220> FEATURE:
<221> NAME/KEY: modified_base
<222> LOCATION: (13)..(13)
<223> OTHER INFORMATION: Oxy-methyl-LNA
<220> FEATURE:
<221> NAME/KEY: modified_base
<222> LOCATION: (14)..(14)
<223> OTHER INFORMATION: Oxy-LNA

<400> SEQUENCE: 35
ctgtttgagg gact                                                       14

<210> SEQ ID NO 36
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(14)
<223> OTHER INFORMATION: Phosphorothioate linkage
<220> FEATURE:
<221> NAME/KEY: modified_base
<222> LOCATION: (1)..(3)
<223> OTHER INFORMATION: Oxy-LNA
<220> FEATURE:
<221> NAME/KEY: modified_base
<222> LOCATION: (12)..(14)
<223> OTHER INFORMATION: Oxy-LNA

<400> SEQUENCE: 36
gagatggcag atgg                                                       14

<210> SEQ ID NO 37
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(14)
<223> OTHER INFORMATION: Phosphorothioate linkage
<220> FEATURE:
<221> NAME/KEY: modified_base
<222> LOCATION: (1)..(1)
<223> OTHER INFORMATION: Oxy-LNA
<220> FEATURE:
<221> NAME/KEY: modified_base
<222> LOCATION: (2)..(2)
<223> OTHER INFORMATION: Oxy-methyl-LNA
<220> FEATURE:
<221> NAME/KEY: modified_base
<222> LOCATION: (3)..(3)
<223> OTHER INFORMATION: Oxy-LNA
<220> FEATURE:
<221> NAME/KEY: modified_base
<222> LOCATION: (12)..(12)
<223> OTHER INFORMATION: Oxy-methyl-LNA
<220> FEATURE:
<221> NAME/KEY: modified_base
<222> LOCATION: (13)..(13)
<223> OTHER INFORMATION: Oxy-LNA
<220> FEATURE:
<221> NAME/KEY: modified_base
<222> LOCATION: (14)..(14)
<223> OTHER INFORMATION: Oxy-methyl-LNA

<400> SEQUENCE: 37
```
gctggtgttg ccac                                              14

<210> SEQ ID NO 38
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(13)
<223> OTHER INFORMATION: Phosphorothioate linkage
<220> FEATURE:
<221> NAME/KEY: modified_base
<222> LOCATION: (1)..(1)
<223> OTHER INFORMATION: Oxy-methyl-LNA
<220> FEATURE:
<221> NAME/KEY: modified_base
<222> LOCATION: (2)..(3)
<223> OTHER INFORMATION: Oxy-LNA
<220> FEATURE:
<221> NAME/KEY: modified_base
<222> LOCATION: (12)..(12)
<223> OTHER INFORMATION: Oxy-LNA
<220> FEATURE:
<221> NAME/KEY: modified_base
<222> LOCATION: (13)..(13)
<223> OTHER INFORMATION: Oxy-methyl-LNA

<400> SEQUENCE: 38
cagatccttg cac                                               13

<210> SEQ ID NO 39
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(14)
<223> OTHER INFORMATION: Phosphorothioate linkage
<220> FEATURE:
<221> NAME/KEY: modified_base
<222> LOCATION: (1)..(2)
<223> OTHER INFORMATION: Oxy-methyl-LNA
<220> FEATURE:
<221> NAME/KEY: modified_base
<222> LOCATION: (3)..(3)
<223> OTHER INFORMATION: Oxy-LNA
<220> FEATURE:
<221> NAME/KEY: modified_base
<222> LOCATION: (12)..(12)
<223> OTHER INFORMATION: Oxy-methyl-LNA
<220> FEATURE:
<221> NAME/KEY: modified_base
<222> LOCATION: (13)..(13)
<223> OTHER INFORMATION: Oxy-LNA
<220> FEATURE:
<221> NAME/KEY: modified_base
<222> LOCATION: (14)..(14)
<223> OTHER INFORMATION: Oxy-methyl-LNA

<400> SEQUENCE: 39
ccagatcctt gcac                                              14

<210> SEQ ID NO 40
<211> LENGTH: 12
<212> TYPE: DNA
<213> ORGANISM: Artificial Sequence
<220> FEATURE:
<223> OTHER INFORMATION: Description of Artificial Sequence: Synthetic

```
      oligonucleotide
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: modified_base
<222> LOCATION: (1)..(1)
<223> OTHER INFORMATION: Oxy-LNA
<220> FEATURE:
<221> NAME/KEY: modified_base
<222> LOCATION: (2)..(2)
<223> OTHER INFORMATION: Oxy-methyl-LNA
<220> FEATURE:
<221> NAME/KEY: modified_base
<222> LOCATION: (11)..(11)
<223> OTHER INFORMATION: Oxy-LNA
<220> FEATURE:
<221> NAME/KEY: modified_base
<222> LOCATION: (12)..(12)
<223> OTHER INFORMATION: Oxy-methyl-LNA

<400> SEQUENCE: 40
accttttgag ac                                                     12

<210> SEQ ID NO 41
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(14)
<223> OTHER INFORMATION: Phosphorothioate linkage
<220> FEATURE:
<221> NAME/KEY: modified_base
<222> LOCATION: (1)..(1)
<223> OTHER INFORMATION: Oxy-methyl-LNA
<220> FEATURE:
<221> NAME/KEY: modified_base
<222> LOCATION: (2)..(3)
<223> OTHER INFORMATION: Oxy-LNA
<220> FEATURE:
<221> NAME/KEY: modified_base
<222> LOCATION: (12)..(12)
<223> OTHER INFORMATION: Oxy-methyl-LNA
<220> FEATURE:
<221> NAME/KEY: modified_base
<222> LOCATION: (13)..(14)
<223> OTHER INFORMATION: Oxy-LNA

<400> SEQUENCE: 41
caatgttcag actg                                                   14

<210> SEQ ID NO 42
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(14)
<223> OTHER INFORMATION: Phosphorothioate linkage
<220> FEATURE:
<221> NAME/KEY: modified_base
<222> LOCATION: (1)..(2)
<223> OTHER INFORMATION: Oxy-methyl-LNA
<220> FEATURE:
<221> NAME/KEY: modified_base
<222> LOCATION: (3)..(3)
<223> OTHER INFORMATION: Oxy-LNA
```

-continued

```
<220> FEATURE:
<221> NAME/KEY: modified_base
<222> LOCATION: (12)..(12)
<223> OTHER INFORMATION: Oxy-methyl-LNA
<220> FEATURE:
<221> NAME/KEY: modified_base
<222> LOCATION: (13)..(14)
<223> OTHER INFORMATION: Oxy-LNA

<400> SEQUENCE: 42
cctgcaatgt tcag                                                           14

<210> SEQ ID NO 43
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(14)
<223> OTHER INFORMATION: Phosphorothioate linkage
<220> FEATURE:
<221> NAME/KEY: modified_base
<222> LOCATION: (1)..(3)
<223> OTHER INFORMATION: Oxy-LNA
<220> FEATURE:
<221> NAME/KEY: modified_base
<222> LOCATION: (12)..(12)
<223> OTHER INFORMATION: Oxy-methyl-LNA
<220> FEATURE:
<221> NAME/KEY: modified_base
<222> LOCATION: (13)..(14)
<223> OTHER INFORMATION: Oxy-LNA

<400> SEQUENCE: 43
tagggctgta gctg                                                           14

<210> SEQ ID NO 44
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(14)
<223> OTHER INFORMATION: Phosphorothioate linkage
<220> FEATURE:
<221> NAME/KEY: modified_base
<222> LOCATION: (1)..(3)
<223> OTHER INFORMATION: Oxy-LNA
<220> FEATURE:
<221> NAME/KEY: modified_base
<222> LOCATION: (12)..(12)
<223> OTHER INFORMATION: Oxy-LNA
<220> FEATURE:
<221> NAME/KEY: modified_base
<222> LOCATION: (13)..(13)
<223> OTHER INFORMATION: Oxy-methyl-LNA
<220> FEATURE:
<221> NAME/KEY: modified_base
<222> LOCATION: (14)..(14)
<223> OTHER INFORMATION: Oxy-LNA

<400> SEQUENCE: 44
gttggtctac ttca                                                           14

<210> SEQ ID NO 45
<211> LENGTH: 14
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(14)
<223> OTHER INFORMATION: Phosphorothioate linkage
<220> FEATURE:
<221> NAME/KEY: modified_base
<222> LOCATION: (1)..(2)
<223> OTHER INFORMATION: Oxy-methyl-LNA
<220> FEATURE:
<221> NAME/KEY: modified_base
<222> LOCATION: (3)..(3)
<223> OTHER INFORMATION: Oxy-LNA
<220> FEATURE:
<221> NAME/KEY: modified_base
<222> LOCATION: (12)..(12)
<223> OTHER INFORMATION: Oxy-methyl-LNA
<220> FEATURE:
<221> NAME/KEY: modified_base
<222> LOCATION: (13)..(13)
<223> OTHER INFORMATION: Oxy-LNA
<220> FEATURE:
<221> NAME/KEY: modified_base
<222> LOCATION: (14)..(14)
<223> OTHER INFORMATION: Oxy-methyl-LNA

<400> SEQUENCE: 45
ccaaccaatt tctc                                                           14

<210> SEQ ID NO 46
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(14)
<223> OTHER INFORMATION: Phosphorothioate linkage
<220> FEATURE:
<221> NAME/KEY: modified_base
<222> LOCATION: (1)..(2)
<223> OTHER INFORMATION: Oxy-LNA
<220> FEATURE:
<221> NAME/KEY: modified_base
<222> LOCATION: (3)..(3)
<223> OTHER INFORMATION: Oxy-methyl-LNA
<220> FEATURE:
<221> NAME/KEY: modified_base
<222> LOCATION: (12)..(14)
<223> OTHER INFORMATION: Oxy-LNA

<400> SEQUENCE: 46
gtcaattgta aagg                                                           14

<210> SEQ ID NO 47
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(14)
<223> OTHER INFORMATION: Phosphorothioate linkage
<220> FEATURE:
<221> NAME/KEY: modified_base
<222> LOCATION: (1)..(3)
<223> OTHER INFORMATION: Oxy-LNA
<220> FEATURE:
```

-continued

```
<221> NAME/KEY: modified_base
<222> LOCATION: (12)..(13)
<223> OTHER INFORMATION: Oxy-methyl-LNA
<220> FEATURE:
<221> NAME/KEY: modified_base
<222> LOCATION: (14)..(14)
<223> OTHER INFORMATION: Oxy-LNA

<400> SEQUENCE: 47
gtttaagaaa tcca                                                      14

<210> SEQ ID NO 48
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: modified_base
<222> LOCATION: (1)..(1)
<223> OTHER INFORMATION: Oxy-methyl-LNA
<220> FEATURE:
<221> NAME/KEY: modified_base
<222> LOCATION: (2)..(2)
<223> OTHER INFORMATION: Oxy-LNA
<220> FEATURE:
<221> NAME/KEY: modified_base
<222> LOCATION: (11)..(11)
<223> OTHER INFORMATION: Oxy-LNA
<220> FEATURE:
<221> NAME/KEY: modified_base
<222> LOCATION: (12)..(12)
<223> OTHER INFORMATION: Oxy-methyl-LNA

<400> SEQUENCE: 48
cttagtgtta gc                                                        12

<210> SEQ ID NO 49
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: modified_base
<222> LOCATION: (1)..(2)
<223> OTHER INFORMATION: Oxy-LNA
<220> FEATURE:
<221> NAME/KEY: modified_base
<222> LOCATION: (11)..(12)
<223> OTHER INFORMATION: Oxy-LNA

<400> SEQUENCE: 49
ggttcttagt gt                                                        12

<210> SEQ ID NO 50
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: misc_feature
<222> LOCATION: (1)..(14)
<223> OTHER INFORMATION: Phosphorothioate linkage
<220> FEATURE:
<221> NAME/KEY: modified_base
<222> LOCATION: (1)..(1)
<223> OTHER INFORMATION: Oxy-methyl-LNA
<220> FEATURE:
<221> NAME/KEY: modified_base
<222> LOCATION: (2)..(3)
<223> OTHER INFORMATION: Oxy-LNA
<220> FEATURE:
<221> NAME/KEY: modified_base
<222> LOCATION: (12)..(14)
<223> OTHER INFORMATION: Oxy-LNA

<400> SEQUENCE: 50
ctggttctta gtgt                                                 14

<210> SEQ ID NO 51
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(13)
<223> OTHER INFORMATION: Phosphorothioate linkage
<220> FEATURE:
<221> NAME/KEY: modified_base
<222> LOCATION: (1)..(1)
<223> OTHER INFORMATION: Oxy-LNA
<220> FEATURE:
<221> NAME/KEY: modified_base
<222> LOCATION: (2)..(2)
<223> OTHER INFORMATION: Oxy-methyl-LNA
<220> FEATURE:
<221> NAME/KEY: modified_base
<222> LOCATION: (11)..(11)
<223> OTHER INFORMATION: Oxy-LNA
<220> FEATURE:
<221> NAME/KEY: modified_base
<222> LOCATION: (12)..(12)
<223> OTHER INFORMATION: Oxy-methyl-LNA
<220> FEATURE:
<221> NAME/KEY: modified_base
<222> LOCATION: (13)..(13)
<223> OTHER INFORMATION: Oxy-LNA

<400> SEQUENCE: 51
gcattggtat tca                                                  13
```

POTENT ANTI APOB ANTISENSE COMPOUNDS

This application is the U.S. national stage under 35 USC §371 of International Application Number PCT/EP2010/058278, filed on Jun. 14, 2010, which claims priority to U.S. Application No. 61/186,388 filed on Jun. 12, 2009; U.S. Application No. 61/253,090 filed on Oct. 20, 2009; and PCT/EP2009/067561, filed Dec. 18, 2009, the entire contents of which applications is hereby incorporated by reference.

SEQUENCE LISTING

The instant application contains a Sequence Listing which has been submitted in ASCII format via EFS-Web and is hereby incorporated by reference in its entirety. Said ASCII copy, created on Oct. 12, 2011, is named 22460US1.txt and is 21,022 bytes in size.

FIELD OF INVENTION

The present invention relates to oligomeric compounds (oligomers), that target APO-100 mRNA in a cell, leading to reduced expression of APO-B100. Reduction of APO-B100 expression is beneficial for a range of medical disorders, such as diseases associated with apolipoproteinB activity, such as in non-limiting example, different types of HDL/LDL cholesterol imbalance; dyslipidemias, e.g., familial combined hyperlipidemia (FCHL), acquired hyperlipidemia, hypercholesterolemia, statin-resistant hypercholesterolemia; coronary artery disease (CAD), coronary heart disease (CHD), atherosclerosis.

RELATED CASES

The following related applications WO2007/031081 and WO2008/113830, are hereby incorporated by reference in their entirety.

BACKGROUND

See the background section of WO2007/031081 and WO2008/113830 which are hereby incorporated by reference.

There remains a need for additional agents which are safe and non-toxic and which are capable of effectively antagonizing apolipoprotein B function and consequently lower plasma Lp(a) levels.

The present invention provides effective and safe Locked Nucleic Acid (LNA) oligomeric compounds and their use in methods for modulating apolipoprotein B expression, ApoB-100, including inhibition of the alternative isoform of apolipoprotein B, ApoB-48.

SUMMARY OF INVENTION

The invention provides an oligomer of between 10-50, such as 10-30 nucleotides in length which comprises a contiguous nucleotide sequence of a total of between 10-30 nucleotides, wherein said contiguous nucleotide sequence is at least 80% (e.g., 85%, 90%, 95%, 98%, or 99%) homologous to a region corresponding to the reverse complement of a mammalian APO-B100 gene or mRNA, such as the human (genbank accession No: NM_000384 or genbank accession No: NG_011793) or naturally occurring variant thereof. Thus, for example, the oligomer hybridizes to a single stranded nucleic acid molecule having the sequence of a portion of APOB-100 mRNA or APOB-100 gene sequences.

The invention provides for a conjugate comprising the oligomer according to the invention, and at least one non-nucleotide or non-polynucleotide moiety covalently attached to said oligomer.

The invention provides for a pharmaceutical composition comprising the oligomer or the conjugate according to the invention, and a pharmaceutically acceptable diluent, carrier, salt or adjuvant.

The invention provides for the oligomer or the conjugate according to invention, for use as a medicament, such as for the treatment of diseases associated with apolipoproteinB activity, such as in non-limiting example, different types of HDL/LDL cholesterol imbalance; dyslipidemias, e.g., familial combined hyperlipidemia (FCHL), acquired hyperlipidemia, hypercholesterolemia, statin-resistant hypercholesterolemia; coronary artery disease (CAD), coronary heart disease (CHD), atherosclerosis.

The invention provides for the use of an oligomer or the conjugate according to the invention, for the manufacture of a medicament for the treatment of diseases associated with apolipoproteinB activity, such as in non-limiting example, different types of HDL/LDL cholesterol imbalance; dyslipidemias, e.g., familial combined hyperlipidemia (FCHL), acquired hyperlipidemia, hypercholesterolemia, statin-resistant hypercholesterolemia; coronary artery disease (CAD), coronary heart disease (CHD), atherosclerosis.

The invention provides for a method of treating diseases associated with apolipoproteinB activity, such as in non-limiting example, different types of HDL/LDL cholesterol imbalance; dyslipidemias, e.g., familial combined hyperlipidemia (FCHL), acquired hyperlipidemia, hypercholesterolemia, statin-resistant hypercholesterolemia; coronary artery disease (CAD), coronary heart disease (CHD), atherosclerosis, said method comprising administering an e.g. effective dose of, an oligomer, a conjugate or a pharmaceutical composition according to the invention, to a patient suffering from, or likely to suffer from diseases associated with apolipoproteinB activity, such as in non-limiting example, different types of HDL/LDL cholesterol imbalance; dyslipidemias, e.g., familial combined hyperlipidemia (FCHL), acquired hyperlipidemia, hypercholesterolemia, statin-resistant hypercholesterolemia; coronary artery disease (CAD), coronary heart disease (CHD), atherosclerosis.

The invention provides for a method for the inhibition of APO-B100 in a cell which is expressing APO-B100, said method comprising administering an oligomer, or a conjugate according to the invention to said cell so as to effect the inhibition of APO-B100 in said cell.

DETAILED DESCRIPTION OF INVENTION

The Oligomer

Figure 1A:
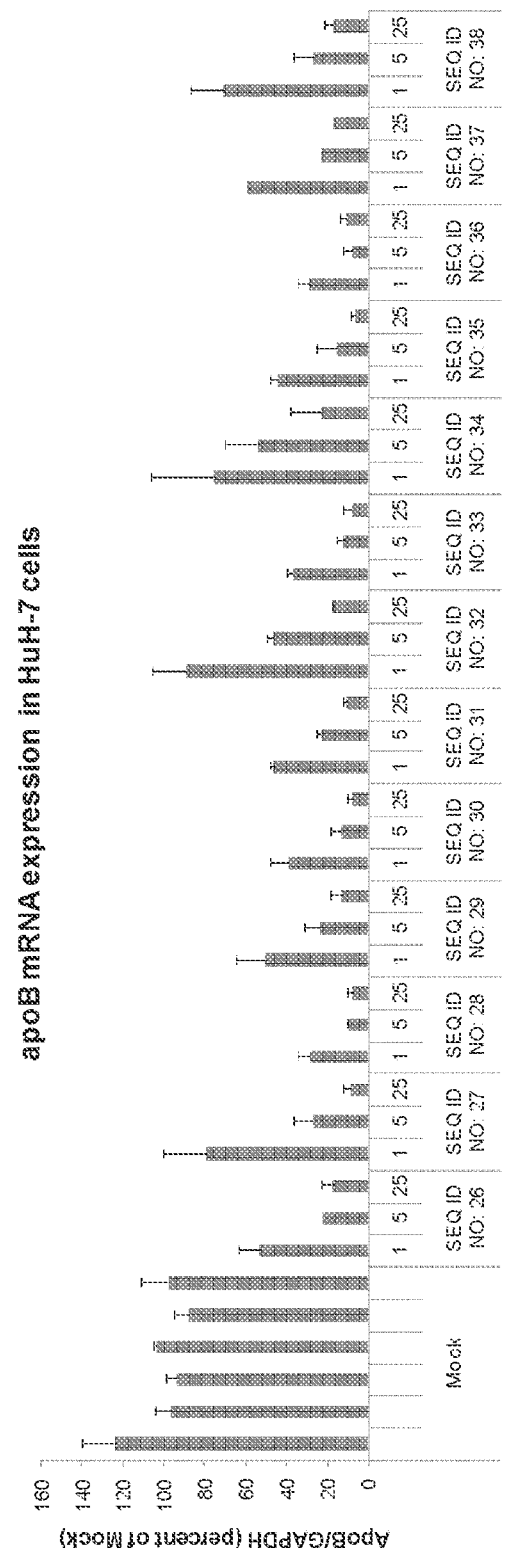
FIG. 1: apoB mRNA expression in HuH-7 cells after treatment with LNA oligonucleotides SEQ ID NOs 26-50. Data are normalised to GAPDH and presented relative to mock control as mean+STD, n=2. A shows SEQ ID NO: 26-38, and B shows SEQ ID NO: 39-50.
Figure 1B:
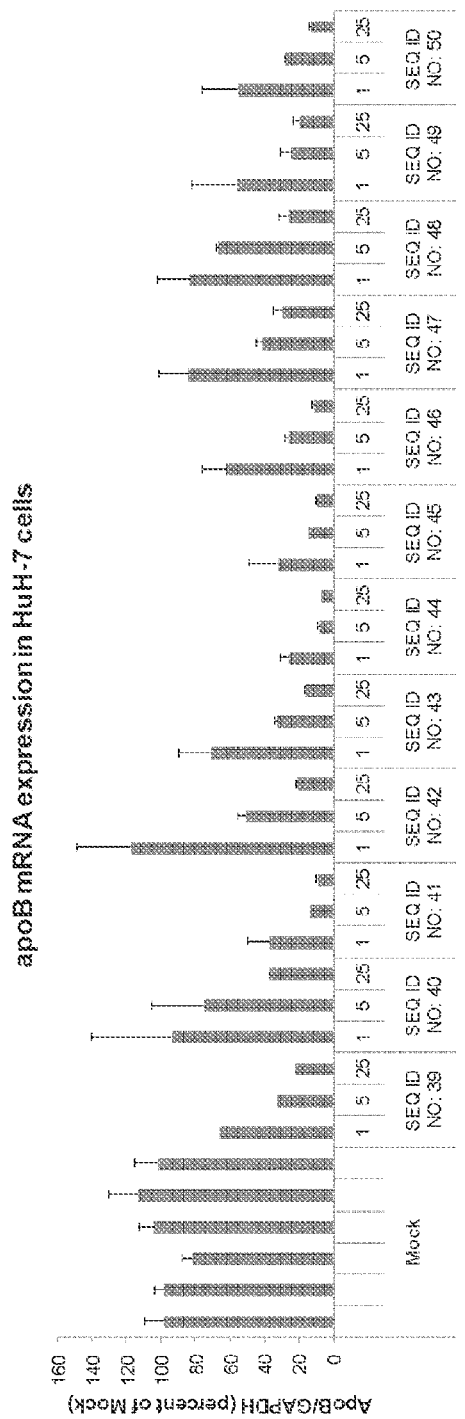

The present invention employs oligomeric compounds (referred herein as oligomers), for use in modulating the function of nucleic acid molecules encoding mammalian APO-B100, such as the APO-B100 nucleic acid of human APO B-100 mRNA or gene, and naturally occurring variants of such nucleic acid molecules encoding mammalian APO-B100. The term "oligomer" in the context of the present invention, refers to a molecule formed by covalent linkage of two or more nucleotides (i.e. an oligonucleotide). Herein, a single nucleotide (unit) may also be referred to as a monomer or unit. The oligomer consists or comprises of a contiguous nucleotide sequence of between 10-50, such as 10-30 nucleotides in length.

In various embodiments, the compound of the invention does not comprise RNA (units). It is preferred that the compound according to the invention is a linear molecule or is synthesised as a linear molecule. The oligomer is a single stranded molecule, and preferably does not comprise short regions of, for example, at least 3, 4 or 5 contiguous nucleotides, which are complementary to equivalent regions within the same oligomer (i.e. duplexes)—in this regards, the oligomer is not (essentially) double stranded. In some embodiments, the oligomer is essentially not double stranded, such as is not a siRNA. In various embodiments, the oligomer of the invention may consist entirely of the contiguous nucleotide region. Thus, the oligomer is not substantially self-complementary.

The Target

Suitably the oligomer of the invention is capable of down-regulating expression of the APO-B100 gene. In this regards, the oligomer of the invention can affect the inhibition of APO-B100, typically in a mammalian such as a human cell, such as liver cells. In some embodiments, the oligomers of the invention bind to the target nucleic acid and effect inhibition of expression of at least 10% or 20% compared to the normal expression level, more preferably at least a 30%, 40%, 50%, 60%, 70%, 80%, 90% or 95% inhibition compared to the normal expression level. In some embodiments, such modulation is seen when using between 0.04 and 25 nM, such as between 0.8 and 20 nM concentration of the compound of the invention. In the same or a different embodiment, the inhibition of expression is less than 100%, such as less than 98% inhibition, less than 95% inhibition, less than 90% inhibition, less than 80% inhibition, such as less than 70% inhibition. Modulation of expression level may be determined by measuring protein levels, e.g. by the methods such as SDS-PAGE followed by western blotting using suitable antibodies raised against the target protein. Alternatively, modulation of expression levels can be determined by measuring levels of mRNA, e.g. by northern blotting or quantitative RT-PCR. When measuring via mRNA levels, the level of down-regulation when using an appropriate dosage, such as between 0.04 and 25 nM, such as between 0.8 and 20 nM concentration, is, in some embodiments, typically to a level of between 10-20% the normal levels in the absence of the compound of the invention.

The invention therefore provides a method of down-regulating or inhibiting the expression of APO-B100 protein and/or mRNA in a cell which is expressing APO-B100 protein and/or mRNA, said method comprising administering the oligomer or conjugate according to the invention to said cell to down-regulating or inhibiting the expression of APO-B100 protein and/or mRNA in said cell. Suitably the cell is a mammalian cell such as a human cell. The administration may occur, in some embodiments, in vitro. The administration may occur, in some embodiments, in vivo.

The term "target nucleic acid", as used herein refers to the DNA or RNA encoding mammalian APO-B100 polypeptide, such as human APO-B100, such as human APO-B100 mRNA. APO-B100 encoding nucleic acids or naturally occurring variants thereof, and RNA nucleic acids derived therefrom, preferably mRNA, such as pre-mRNA, although preferably mature mRNA. In some embodiments, for example when used in research or diagnostics the "target nucleic acid" may be a cDNA or a synthetic oligonucleotide derived from the above DNA or RNA nucleic acid targets. The oligomer according to the invention is preferably capable of hybridising to the target nucleic acid. It will be recognised that human APO-B100 mRNA is a cDNA sequences, and as such, corresponds to the mature mRNA target sequence, although uracil is replaced with thymidine in the cDNA sequences.

The term "naturally occurring variant thereof" refers to variants of the APO-B100 polypeptide of nucleic acid sequence which exist naturally within the defined taxonomic group, such as mammalian, such as mouse, monkey, and preferably human. Typically, when referring to "naturally occurring variants" of a polynucleotide the term also may encompass any allelic variant of the APO-B100 encoding genomic DNA by chromosomal translocation or duplication, and the RNA, such as mRNA derived therefrom. "Naturally occurring variants" may also include variants derived from alternative splicing of the APO-B100 mRNA. When referenced to a specific polypeptide sequence, e.g., the term also includes naturally occurring forms of the protein which may therefore be processed, e.g. by co- or post-translational modifications, such as signal peptide cleavage, proteolytic cleavage, glycosylation, etc.

Sequences

The oligomers comprise or consist of a contiguous nucleotide sequence which corresponds to the reverse complement of a nucleotide sequence present in human APO-B100 mRNA. Thus, the oligomer can comprise or consist of, or a sequence selected from the group consisting of SEQ ID NOS: 1-25 (Table 1), wherein said oligomer (or contiguous nucleotide portion thereof) may optionally have one, two, or three mismatches against said selected sequence.

TABLE 1

| Test substance | Length | Target seq |
|---|---|---|
| SEQ ID NO: 1 | 14 | 5'-TCTGAAGTCCATGA-3' |
| SEQ ID NO: 2 | 14 | 5'-GGATCAAATATAAG-3' |

TABLE 1-continued

| Test substance | Length | Target seq |
|---|---|---|
| SEQ ID NO: 3 | 14 | 5'-GTTGACACTGTCTG-3' |
| SEQ ID NO: 4 | 12 | 5'-GTTGACACTGTC-3' |
| SEQ ID NO: 5 | 14 | 5'-GACTGCCTGTTCTC-3' |
| SEQ ID NO: 6 | 13 | 5'-CGTTGGAGTAAGC-3' |
| SEQ ID NO: 7 | 14 | 5'-GCGTTGGAGTAAGC-3' |
| SEQ ID NO: 8 | 14 | 5'-CTCTGTGATCCAGG-3' |
| SEQ ID NO: 9 | 14 | 5'-GGACTCTGTGATCC-3' |
| SEQ ID NO: 10 | 14 | 5'-CTGTTTGAGGGACT-3' |
| SEQ ID NO: 11 | 14 | 5'-GAGATGGCAGATGG-3' |
| SEQ ID NO: 12 | 14 | 5'-GCTGGTGTTGCCAC-3' |
| SEQ ID NO: 13 | 13 | 5'-CAGATCCTTGCAC-3' |
| SEQ ID NO: 14 | 14 | 5'-CCAGATCCTTGCAC-3' |
| SEQ ID NO: 15 | 12 | 5'-ACCTTTTGAGAC-3' |
| SEQ ID NO: 16 | 14 | 5'-CAATGTTCAGACTG-3' |
| SEQ ID NO: 17 | 14 | 5'-CCTGCAATGTTCAG-3' |
| SEQ ID NO: 18 | 14 | 5'-TAGGGCTGTAGCTG-3' |
| SEQ ID NO: 19 | 14 | 5'-GTTGGTCTACTTCA-3' |
| SEQ ID NO: 20 | 14 | 5'-CCAACCAATTTCTC-3' |
| SEQ ID NO: 21 | 14 | 5'-GTCAATTGTAAAGG-3' |
| SEQ ID NO: 22 | 14 | 5'-GTTTAAGAAATCCA-3' |
| SEQ ID NO: 23 | 12 | 5'-CTTAGTGTTAGC-3' |
| SEQ ID NO: 24 | 12 | 5'-GGTTCTTAGTGT-3' |
| SEQ ID NO: 25 | 14 | 5'-CTGGTTCTTAGTGT-3' |

The oligomer may comprise or consist of a contiguous nucleotide sequence which is fully complementary (perfectly complementary) to the equivalent region of a nucleic acid which encodes a mammalian APO-B100 (e.g., human APO-B100 mRNA). Thus, the oligomer can comprise or consist of an antisense nucleotide sequence.

However, in some embodiments, the oligomer may tolerate 1, 2, 3, or 4 (or more) mismatches, when hybridising to the target sequence and still sufficiently bind to the target to show the desired effect, i.e. down-regulation of the target. Mismatches may, for example, be compensated by increased length of the oligomer nucleotide sequence and/or an increased number of nucleotide analogues, such as LNA, present within the nucleotide sequence.

In some embodiments, the contiguous nucleotide sequence comprises no more than 3, such as no more than 2 mismatches when hybridizing to the target sequence, such as to the corresponding region of a nucleic acid which encodes a mammalian APO-B100.

In some embodiments, the contiguous nucleotide sequence comprises no more than a single mismatch when hybridizing to the target sequence, such as the corresponding region of a nucleic acid which encodes a mammalian APO-B100.

The nucleotide sequence of the oligomers of the invention or the contiguous nucleotide sequence is preferably at least 80% homologous to a corresponding sequence selected from the group consisting of SEQ ID NOS: 1-25, such as at least 85%, at least 90%, at least 91%, at least 92%, at least 93%, at least 94%, at least 95%, at least 96% homologous, such as 100% homologous (identical).

The nucleotide sequence of the oligomers of the invention or the contiguous nucleotide sequence is preferably at least 80% homologous to the reverse complement of a corresponding sequence present in human APO-B100 mRNA, such as at least 85%, at least 90%, at least 91%, at least 92% at least 93%, at least 94%, at least 95%, at least 96% homologous, such as 100% homologous (identical).

The nucleotide sequence of the oligomers of the invention or the contiguous nucleotide sequence is preferably at least 80% complementary to a sub-sequence present in human APO-B100 mRNA, such as at least 85%, at least 90%, at least 91%, at least 92%, at least 93%, at least 94%, at least 95%, at least 96% complementary, such as 100% complementary (perfectly complementary).

In some embodiments the oligomer (or contiguous nucleotide portion thereof) is selected from, or comprises, one of the sequences selected from the group consisting of SEQ ID NOS: 1-25, or a sub-sequence of at least 10 contiguous nucleotides thereof, wherein said oligomer (or contiguous nucleotide portion thereof) may optionally comprise one, two, or three mismatches when compared to the sequence.

However, it is recognised that, in some embodiments the nucleotide sequence of the oligomer may comprise additional 5' or 3' nucleotides, such as, independently, 1, 2, 3, 4 or 5 additional nucleotides 5' and/or 3', which are non-complementary to the target sequence. In this respect the oligomer of the invention, may, in some embodiments, comprise a contiguous nucleotide sequence which is flanked 5' and or 3' by additional nucleotides. In some embodiments the additional 5' or 3' nucleotides are naturally occurring nucleotides, such as DNA or RNA. In some embodiments, the additional 5' or 3' nucleotides may represent region D as referred to in the context of gapmer oligomers herein.

In some embodiments the oligomer according to the invention consists or comprises of a nucleotide sequence according to SEQ ID NO:3, or a sub-sequence of thereof.

In some embodiments the oligomer according to the invention consists or comprises of a nucleotide sequence according to SEQ ID NO:4, or a sub-sequence of thereof.

In some embodiments the oligomer according to the invention consists or comprises of a nucleotide sequence according to SEQ ID NO:19, or a sub-sequence of thereof.

In some embodiments the oligomer according to the invention consists or comprises of a nucleotide sequence according to SEQ ID NO:20, or a sub-sequence of thereof.

When determining "homology" between the oligomers of the invention (or contiguous nucleotide sequence) and the nucleic acid which encodes the mammalian APO-B100 or the reverse complement thereof, such as those disclosed herein, the determination of homology may be made by a simple alignment with the corresponding nucleotide sequence of the compound of the invention and the corresponding region of the nucleic acid which encodes the mammalian APO-B100 (or target nucleic acid), or the reverse complement thereof, and the homology is determined by counting the number of bases which align and dividing by the total number of contiguous nucleotides in the compound of the invention, and multiplying by 100. In such a comparison, if gaps exist, it is preferable that such gaps are merely mismatches rather than areas where the number of nucleotides within the gap differs between the nucleotide sequence of the invention and the target nucleic acid.

The terms "corresponding to" and "corresponds to" refer to the comparison between the nucleotide sequence of the oligomer or contiguous nucleotide sequence (a first sequence) and the equivalent contiguous nucleotide sequence of a further sequence selected from either i) a sub-sequence of the reverse complement of the nucleic acid target, such as the mRNA which encodes the APO-B100 protein, such as human APO-B100 mRNA, and/or ii) the sequence of nucleotides provided herein such as the group consisting of SEQ ID NOS: 3, 4, 19 or 20, or sub-sequence thereof. Nucleotide analogues are compared directly to their equivalent or corresponding nucleotides. A first sequence which corresponds to a further sequence under i) or ii) typically is identical to that sequence over the length of the first sequence (such as the contiguous nucleotide sequence) or, as described herein may, in some embodiments, is at least 80% homologous to a corresponding sequence, such as at least 85%, at least 90%, at least 91%, at least 92% at least 93%, at least 94%, at least 95%, at least 96% homologous, such as 100% homologous (identical).

The terms "corresponding nucleotide analogue" and "corresponding nucleotide" are intended to indicate that the nucleotide in the nucleotide analogue and the naturally occurring nucleotide are identical. For example, when the 2-deoxyribose unit of the nucleotide is linked to an adenine, the "corresponding nucleotide analogue" contains a pentose unit (different from 2-deoxyribose) linked to an adenine.

Length

The oligomers may comprise or consist of a contiguous nucleotide sequence of a total of between 10, 11, 12, 13, 14, 15, 16, 17, 18, 19, 20, 21, 22, 23, 24, 25, 26, 27, 28, 29 or 30 contiguous nucleotides in length.

In some embodiments, the oligomers comprise or consist of a contiguous nucleotide sequence of a total of between 10-22, such as 12-18, such as 13-17 or 12-16, such as 13, 14, 15, 16 contiguous nucleotides in length.

In some embodiments, the oligomers comprise or consist of a contiguous nucleotide sequence of a total of 10, 11, 12, 13, or 14 contiguous nucleotides in length.

In some embodiments, the oligomer according to the invention consists of no more than 22 nucleotides, such as no more than 20 nucleotides, such as no more than 18 nucleotides, such as 15, 16 or 17 nucleotides. In some embodiments the oligomer of the invention comprises less than 20 nucleotides.

Nucleotide Analogues

The term "nucleotide" as used herein, refers to a glycoside comprising a sugar moiety, a base moiety and a covalently linked phosphate group and covers both naturally occurring nucleotides, such as DNA or RNA, preferably DNA, and non-naturally occurring nucleotides comprising modified sugar and/or base moieties, which are also referred to as "nucleotide analogues" herein.

Non-naturally occurring nucleotides include nucleotides which have modified sugar moieties, such as bicyclic nucleotides or 2' modified nucleotides, such as 2' substituted nucleotides.

"Nucleotide analogues" are variants of natural nucleotides, such as DNA or RNA nucleotides, by virtue of modifications in the sugar and/or base moieties. Analogues could in principle be merely "silent" or "equivalent" to the natural nucleotides in the context of the oligonucleotide, i.e. have no functional effect on the way the oligonucleotide works to inhibit target gene expression. Such "equivalent" analogues may nevertheless be useful if, for example, they are easier or cheaper to manufacture, or are more stable to storage or manufacturing conditions, or represent a tag or label. Preferably, however, the analogues will have a functional effect on the way in which the oligomer works to inhibit expression; for example by producing increased binding affinity to the target and/or increased resistance to intracellular nucleases and/or increased ease of transport into the cell. Specific examples of nucleoside analogues are described by e.g. Freier & Altmann; *Nucl. Acid Res.*, 1997, 25, 4429-4443 and Uhlmann; *Curr. Opinion in Drug Development*, 2000, 3(2), 293-213, and in Scheme 1:

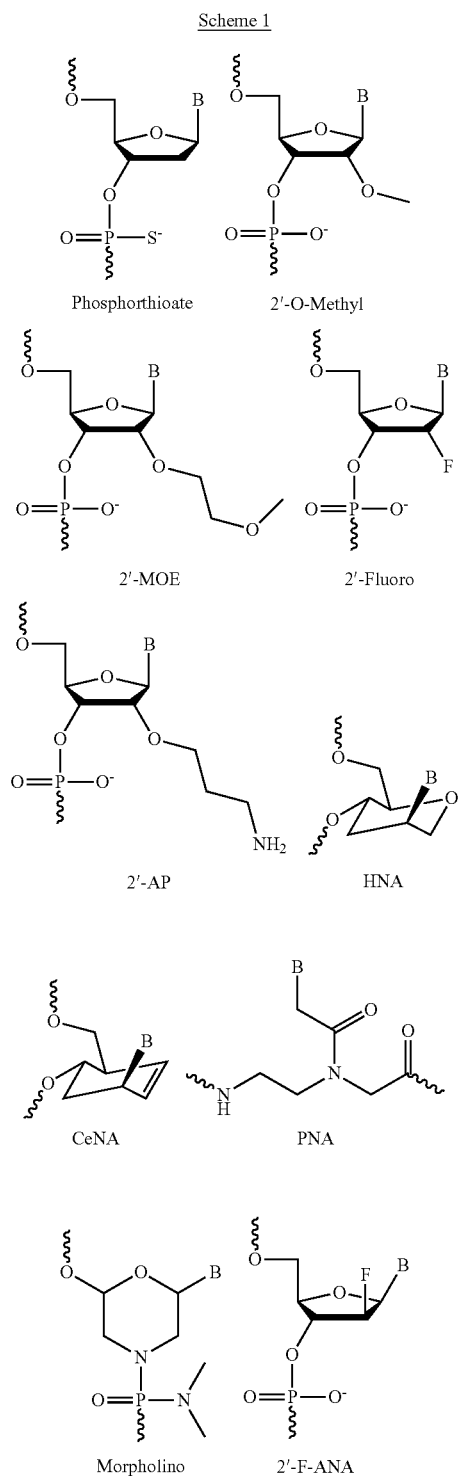

Scheme 1

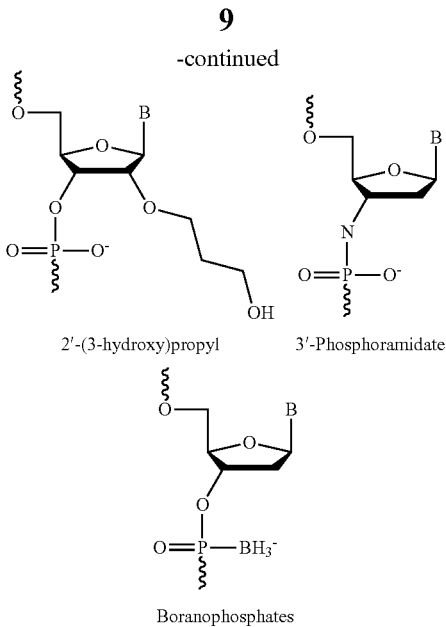

2'-(3-hydroxy)propyl    3'-Phosphoramidate

Boranophosphates

The oligomer may thus comprise or consist of a simple sequence of natural occurring nucleotides—preferably 2'-deoxynucleotides (referred to here generally as "DNA"), but also possibly ribonucleotides (referred to here generally as "RNA"), or a combination of such naturally occurring nucleotides and one or more non-naturally occurring nucleotides, i.e. nucleotide analogues. Such nucleotide analogues may suitably enhance the affinity of the oligomer for the target sequence.

Examples of suitable and preferred nucleotide analogues are provided by PCT/DK2006/000512 or are referenced therein.

Incorporation of affinity-enhancing nucleotide analogues in the oligomer, such as LNA or 2'-substituted sugars, can allow the size of the specifically binding oligomer to be reduced, and may also reduce the upper limit to the size of the oligomer before non-specific or aberrant binding takes place.

In some embodiments the oligomer comprises at least 2 nucleotide analogues. In some embodiments, the oligomer comprises from 3-8 nucleotide analogues, e.g. 6 or 7 nucleotide analogues. In the by far most preferred embodiments, at least one of said nucleotide analogues is a locked nucleic acid (LNA); for example at least 3 or at least 4, or at least 5, or at least 6, or at least 7, or 8, of the nucleotide analogues may be LNA. In some embodiments all the nucleotides analogues may be LNA.

It will be recognised that when referring to a preferred nucleotide sequence motif or nucleotide sequence, which consists of only nucleotides, the oligomers of the invention which are defined by that sequence may comprise a corresponding nucleotide analogue in place of one or more of the nucleotides present in said sequence, such as LNA units or other nucleotide analogues, which raise the duplex stability/$T_m$ of the oligomer/target duplex (i.e. affinity enhancing nucleotide analogues).

In some embodiments, any mismatches between the nucleotide sequence of the oligomer and the target sequence are preferably found in regions outside the affinity enhancing nucleotide analogues, such as region B as referred to herein, and/or region D as referred to herein, and/or at the site of non modified such as DNA nucleotides in the oligonucleotide, and/or in regions which are 5' or 3' to the contiguous nucleotide sequence.

Examples of such modification of the nucleotide include modifying the sugar moiety to provide a 2'-substituent group or to produce a bridged (locked nucleic acid) structure which enhances binding affinity and may also provide increased nuclease resistance.

A preferred nucleotide analogue is LNA, such as oxy-LNA (such as beta-D-oxy-LNA, and alpha-L-oxy-LNA), and/or amino-LNA (such as beta-D-amino-LNA and alpha-L-amino-LNA) and/or thio-LNA (such as beta-D-thio-LNA and alpha-L-thio-LNA) and/or ENA (such as beta-D-ENA and alpha-L-ENA). Most preferred is beta-D-oxy-LNA.

In some embodiments the nucleotide analogues present within the oligomer of the invention (such as in regions A and C mentioned herein) are independently selected from, for example: 2'-O-alkyl-RNA units, 2'-amino-DNA units, 2'-fluoro-DNA units, LNA units, arabino nucleic acid (ANA) units, 2'-fluoro-ANA units, HNA units, INA (intercalating nucleic acid—Christensen, 2002. Nucl. Acids. Res. 2002 30: 4918-4925, hereby incorporated by reference) units and 2'MOE units. In some embodiments there is only one of the above types of nucleotide analogues present in the oligomer of the invention, or contiguous nucleotide sequence thereof.

In some embodiments the nucleotide analogues are 2'-O-methoxyethyl-RNA (2'MOE), 2'-fluoro-DNA monomers or LNA nucleotide analogues, and as such the oligonucleotide of the invention may comprise nucleotide analogues which are independently selected from these three types of analogue, or may comprise only one type of analogue selected from the three types. In some embodiments at least one of said nucleotide analogues is 2'-MOE-RNA, such as 2, 3, 4, 5, 6, 7, 8, 9 or 10 2'-MOE-RNA nucleotide units. In some embodiments at least one of said nucleotide analogues is 2'-fluoro DNA, such as 2, 3, 4, 5, 6, 7, 8, 9 or 10 2'-fluoro-DNA nucleotide units.

In some embodiments, the oligomer according to the invention comprises at least one Locked Nucleic Acid (LNA) unit, such as 1, 2, 3, 4, 5, 6, 7, or 8 LNA units, such as between 3-7 or 4 to 8 LNA units, or 3, 4, 5, 6 or 7 LNA units. In some embodiments, all the nucleotide analogues are LNA. In some embodiments, the oligomer may comprise both beta-D-oxy-LNA, and one or more of the following LNA units: thio-LNA, amino-LNA, oxy-LNA, and/or ENA in either the beta-D or alpha-L configurations or combinations thereof. In some embodiments all LNA cytosine units are 5'methyl-Cytosine. In some embodiments of the invention, the oligomer may comprise both LNA and DNA units. Preferably the combined total of LNA and DNA units is 10-25, preferably 10-20, even more preferably 12-16. In some embodiments of the invention, the nucleotide sequence of the oligomer, such as the contiguous nucleotide sequence consists of at least one LNA and the remaining nucleotide units are DNA units. In some embodiments the oligomer comprises only LNA nucleotide analogues and naturally occurring nucleotides (such as RNA or DNA, most preferably DNA nucleotides), optionally with modified internucleotide linkages such as phosphorothioate.

The term "nucleobase" refers to the base moiety of a nucleotide and covers both naturally occurring a well as non-naturally occurring variants. Thus, "nucleobase" covers not only the known purine and pyrimidine heterocycles but also heterocyclic analogues and tautomeres thereof.

Examples of nucleobases include, but are not limited to adenine, guanine, cytosine, thymidine, uracil, xanthine, hypoxanthine, 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

In some embodiments, at least one of the nucleobases present in the oligomer is a modified nucleobase selected from the group consisting of 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

LNA

The term "LNA" refers to a bicyclic nucleotide analogue, known as "Locked Nucleic Acid". It may refer to an LNA monomer, or, when used in the context of an "LNA oligonucleotide", LNA refers to an oligonucleotide containing one or more such bicyclic nucleotide analogues. LNA nucleotides are characterised by the presence of a biradical 'bridge' between C2' and C4' of the ribose sugar ring—for example as shown as the biradical $R^{4*}$—$R^{2*}$ as described below.

The LNA used in the oligonucleotide compounds of the invention preferably has the structure of the general formula I

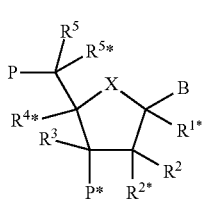

Formula 1 wherein for all chiral centers, asymmetric groups may be found in either R or S orientation;

wherein X is selected from —O—, —S—, —N($R^{N*}$)—, —C($R^6 R^{6*}$)—, such as, in some embodiments —O—;

B is selected from hydrogen, optionally substituted $C_{1-4}$-alkoxy, optionally substituted $C_{1-4}$-alkyl, optionally substituted $C_{1-4}$-acyloxy, nucleobases including naturally occurring and nucleobase analogues, DNA intercalators, photochemically active groups, thermochemically active groups, chelating groups, reporter groups, and ligands;

P designates an internucleotide linkage to an adjacent monomer, or a 5'-terminal group, such internucleotide linkage or 5'-terminal group optionally including the substituent $R^5$ or equally applicable the substituent $R^{5*}$;

P* designates an internucleotide linkage to an adjacent monomer, or a 3'-terminal group;

$R^{4*}$ and $R^{2*}$ together designate a biradical consisting of 1-4 groups/atoms selected from —C($R^a R^b$)—, —C($R^a$)=C($R^b$)—, —C($R^a$)=N—, —O—, —Si($R^a$)$_2$—, —S—, —SO$_2$—, —N($R^a$)—, and >C=Z, wherein Z is selected from —O—, —S—, and —N($R^a$)—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, optionally substituted $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=CH$_2$), wherein for all chiral centers, asymmetric groups may be found in either R or S orientation, and;

each of the substituents $R^{1*}$, $R^2$, $R^3$, $R^5$, $R^{5*}$, $R^6$ and $R^{6*}$, which are present is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene; wherein $R^N$ is selected from hydrogen and $C_{1-4}$-alkyl, and where two adjacent (non-geminal) substituents may designate an additional bond resulting in a double bond; and $R^{N*}$, when present and not involved in a biradical, is selected from hydrogen and $C_{1-4}$-alkyl; and basic salts and acid addition salts thereof. For all chiral centers, asymmetric groups may be found in either R or S orientation.

In some embodiments, $R^{4*}$ and $R^{2*}$ together designate a biradical consisting of a groups selected from the group consisting of C($R^a R^b$)—C($R^a R^b$)—, C($R^a R^b$)—O—, C($R^a R^b$)—NR$^a$—, C($R^a R^b$)—S—, and C($R^a R^b$)—C($R^a R^b$)—O—, wherein each $R^a$ and $R^b$ may optionally be independently selected. In some embodiments, $R^a$ and $R^b$ may be, optionally independently selected from the group consisting of hydrogen and $_{C1-6}$-alkyl, such as methyl, such as hydrogen.

In some embodiments, $R^{1*}$, $R^2$, $R^3$, $R^5$, $R^{5*}$ are independently selected from the group consisting of hydrogen, halogen, $C_{1-6}$alkyl, substituted $C_{1-6}$alkyl, $C_{2-6}$alkenyl, substituted $C_{2-6}$alkenyl, $C_{2-6}$alkynyl or substituted $C_{2-6}$alkynyl, $C_{1-6}$alkoxyl, substituted $C_{1-6}$alkoxyl, acyl, substituted acyl, $C_{1-6}$ aminoalkyl or substituted $C_{1-6}$ aminoalkyl. For all chiral centers, asymmetric groups may be found in either R or S orientation.

In some embodiments, $R^{1*}$, $R^2$, $R^3$, $R^5$, $R^{5*}$ are hydrogen.

In some embodiments, $R^{1*}$, $R^2$, $R^3$ are independently selected from the group consisting of hydrogen, halogen, $C_{1-6}$alkyl, substituted $C_{1-6}$alkyl, $C_{2-6}$alkenyl, substituted $C_{2-6}$alkenyl, $C_{2-6}$alkynyl or substituted $C_{2-6}$alkynyl, $C_{1-6}$alkoxyl, substituted $C_{1-6}$alkoxyl, acyl, substituted acyl, $C_{1-6}$ aminoalkyl or substituted $C_{1-6}$ aminoalkyl. For all chiral centers, asymmetric groups may be found in either R or S orientation.

In some embodiments, $R^{1*}$, $R^2$, $R^3$ are hydrogen.

In some embodiments, $R^5$ and $R^{5*}$ are each independently selected from the group consisting of H, —CH$_3$, —CH$_2$—CH$_3$, CH$_2$—O—CH$_3$, and —CH=CH$_2$. Suitably in some embodiments, either $R^5$ or $R^{5*}$ are hydrogen, where as the other group ($R^5$ or $R^{5*}$ respectively) is selected from the group consisting of $C_{1-5}$alkyl, $C_{2-6}$alkenyl, $C_{2-6}$alkynyl, substituted $C_{1-6}$alkyl, substituted $C_{2-6}$alkenyl, substituted $C_{2-6}$alkynyl or substituted acyl (—C(=O)—); wherein each substituted group is mono or poly substituted with substituent groups independently selected from halogen, $C_{1-6}$alkyl, substituted $C_{1-6}$alkyl, $C_{2-6}$alkenyl, substituted $C_{2-6}$alkenyl, $C_{2-6}$alkynyl, substituted $C_{2-6}$alkynyl, $OJ_1$, $SJ_1$, $NJ_1J_2$, $N_3$, $COOJ_1$, CN, O—C(=O)$NJ_1J_2$, N(H)C(=NH)NR, $R_2$ or N(H)C(=X)N (H)$J_2$ wherein X is O or S; and each $J_1$ and $J_2$ is, independently, H, $C_{1-6}$alkyl, substituted $C_{1-6}$alkyl, $C_{2-6}$alkenyl, substituted $C_{2-6}$alkenyl, $C_{2-6}$alkynyl, substituted $C_{2-6}$alkynyl, $C_{1-6}$ aminoalkyl, substituted $C_{1-6}$ aminoalkyl or a protecting group. In some embodiments either $R^5$ or $R^{5*}$ is substituted $C_{1-6}$alkyl. In some embodiments either $R^5$ or $R^{5*}$ is substituted methylene wherein preferred substituent groups include one or more groups independently selected from F, $NJ_1J_2$, $N_3$, CN, $OJ_1$, $SJ_1$, O—C(=O)$NJ_1J_2$, N(H)C(=NH)$NJ$, $J_2$ or N(H)C(O)N(H)$J_2$. In some embodiments each $J_1$ and $J_2$ is, independently H or $C_{1-6}$alkyl. In some embodiments either $R^5$ or $R^{5*}$ is methyl, ethyl or methoxymethyl. In some embodiments either $R^5$ or $R^{5*}$ is methyl. In a further embodiment either $R^5$ or $R^{5*}$ is ethylenyl. In some embodiments either $R^5$ or $R^{5*}$ is substituted acyl. In some embodiments either $R^5$ or $R^{5*}$ is C(=O)$NJ_1J_2$. For all chiral centers, asymmetric groups may be found in either R or S orientation. Such 5' modified bicyclic nucleotides are disclosed in WO 2007/134181, which is hereby incorporated by reference in its entirety.

In some embodiments B is a nucleobase, including nucleobase analogues and naturally occurring nucleobases, such as a purine or pyrimidine, or a substituted purine or substituted pyrimidine, such as a nucleobase referred to herein, such as a nucleobase selected from the group consisting of adenine, cytosine, thymine, adenine, uracil, and/or a modified or substituted nucleobase, such as 5-thiazolo-uracil, 2-thio-uracil, 5-propynyl-uracil, 2'thio-thymine, 5-methyl cytosine, 5-thiozolo-cytosine, 5-propynyl-cytosine, and 2,6-diaminopurine.

In some embodiments, $R^{4*}$ and $R^{2*}$ together designate a biradical selected from —C($R^aR^b$)—O—, —C($R^aR^b$)—C($R^cR^d$)—O, —C($R^aR^b$)—C($R^cR^d$)—C($R^eR^f$)—O—, —C($R^aR^b$)—O—C($R^cR^d$)—, —C($R^aR^b$)—O—C($R^cR^d$)—O—, —C($R^aR^b$)—C($R^cR^d$)—, —C($R^aR^b$)—C($R^cR^d$)—C($R^eR^f$)—, —C($R^a$)=C($R^b$)—C($R^cR^d$)—, —C($R^aR^b$)—N($R^c$)—, —C($R^aR^b$)—C($R^cR^d$)—N($R^e$)—, —C($R^aR^b$)—N($R^c$)—O—, —C($R^aR^b$)—S—, —C($R^aR^b$)—C($R^cR^d$)—S—, wherein $R^a$, $R^b$, $R^c$, $R^d$, $R^e$, and $R^f$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl) amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=$CH_2$). For all chiral centers, asymmetric groups may be found in either R or S orientation.

In a further embodiment $R^{4*}$ and $R^{2*}$ together designate a biradical (bivalent group) selected from —$CH_2$—O—, —$CH_2$—S—, —$CH_2$—NH—, —$CH_2$—N($CH_3$)—, —$CH_2$—$CH_2$—O—, —$CH_2$—CH($CH_3$)—, —$CH_2$—$CH_2$—S—, —$CH_2$—$CH_2$—NH—, —$CH_2$—$CH_2$—$CH_2$—, —$CH_2$—$CH_2$—$CH_2$—O—, —$CH_2$—$CH_2$—CH($CH_3$)—, —CH=CH—$CH_2$—, —$CH_2$—O—$CH_2$—O—, —$CH_2$—NH—O—, —$CH_2$—N($CH_3$)—O—, —$CH_2$—O—$CH_2$—, —CH($CH_3$)—O—, and —CH($CH_2$—O—$CH_3$)—O—, and/or, —$CH_2$—$CH_2$—, and —CH=CH—. For all chiral centers, asymmetric groups may be found in either R or S orientation.

In some preferred embodiments, $R^{4*}$ and $R^{2*}$ together designate the biradical —O—CH($CH_2OCH_3$)—(2'O-methoxyethyl bicyclic nucleic acid—Seth at al., 2010, J. Org. Chem)—in either the R- or S-configuration.

In some preferred embodiments, $R^{4*}$ and $R^{2*}$ together designate the biradical —O—CH($CH_2CH_3$)—(2'O-ethyl bicyclic nucleic acid—Seth at al., 2010, J. Org. Chem).—in either the R- or S-configuration.

In some preferred embodiments, $R^{4*}$ and $R^{2*}$ together designate the biradical —O—CH($CH_3$)—.—in either the R- or S-configuration. In some embodiments, $R^{4*}$ and $R^{2*}$ together designate the biradical C($R^aR^b$)—N($R^c$)—O—, wherein $R^a$ and $R^b$ are independently selected from the group consisting of hydrogen, halogen, $C_{1-6}$alkyl, substituted $C_{1-6}$alkyl, $C_{2-6}$alkenyl, substituted $C_{2-6}$alkenyl, $C_{2-6}$alkynyl or substituted $C_{2-6}$alkynyl, $C_{1-6}$alkoxyl, substituted $C_{1-6}$alkoxyl, acyl, substituted acyl, $C_{1-6}$ aminoalkyl or substituted $C_{1-6}$ aminoalkyl, such as hydrogen, and; wherein $R^c$ is selected from the group consisting of hydrogen, halogen, $C_{2-6}$alkyl, substituted $C_{1-6}$alkyl, $C_{1-6}$alkenyl, substituted $C_{2-6}$alkenyl, $C_{2-6}$alkynyl or substituted $C_{2-6}$alkynyl, $C_{1-6}$alkoxyl, substituted $C_{1-6}$alkoxyl, acyl, substituted acyl, $C_{1-6}$ aminoalkyl or substituted $C_{1-6}$ aminoalkyl, such as hydrogen.

In some embodiments, $R^{4*}$ and $R^{2*}$ together designate the biradical C($R^aR^b$)—O—C($R^cR^d$)—O—, wherein $R^a$, $R^b$, $R^c$, and $R^d$ are independently selected from the group consisting of hydrogen, halogen, $C_{1-6}$alkyl, substituted $C_{1-6}$alkyl, $C_{2-6}$alkenyl, substituted $C_{2-6}$alkenyl, $C_{2-6}$alkynyl or substituted $C_{2-6}$alkynyl, $C_{1-6}$alkoxyl, substituted $C_{1-6}$alkoxyl, acyl, substituted acyl, $C_{1-6}$ aminoalkyl or substituted $C_{1-6}$ aminoalkyl, such as hydrogen.

In some embodiments, $R^{4*}$ and $R^{2*}$ form the biradical —CH(Z)—O—, wherein Z is selected from the group consisting of $C_{1-6}$alkyl, $C_{2-6}$alkenyl, $C_{2-6}$alkynyl, substituted $C_{1-6}$alkyl, substituted $C_{2-6}$alkenyl, substituted $C_{2-6}$alkynyl, acyl, substituted acyl, substituted amide, thiol or substituted thio; and wherein each of the substituted groups, is, independently, mono or poly substituted with optionally protected substituent groups independently selected from halogen, oxo, hydroxyl, $OJ_1$, $NJ_1J_2$, $SJ_1$, $N_3$, OC(=X)$J_1$, OC(=X)$NJ_1J_2$, $NJ^3C$(=X)$NJ_1J_2$ and CN, wherein each $J_1$, $J_2$ and $J_3$ is, independently, H or $C_{1-6}$alkyl, and X is O, S or $NJ_1$. In some embodiments Z is $C_{1-6}$alkyl or substituted $C_{1-6}$alkyl. In some embodiments Z is methyl. In some embodiments Z is substituted $C_{1-6}$alkyl. In some embodiments said substituent group is $C_{1-6}$alkoxy. In some embodiments Z is $CH_3OCH_2$—. For all chiral centers, asymmetric groups may be found in either R or S orientation. Such bicyclic nucleotides are disclosed in U.S. Pat. No. 7,399,845 which is hereby incorporated by reference in its entirety. In some embodiments, $R^{1*}$, $R^2$, $R^3$, $R^5$, $R^{5*}$ are hydrogen. In some some embodiments, $R^{1*}$, $R^2$, $R^{3*}$ are hydrogen, and one or both of $R^5$, $R^{5*}$ may be other than hydrogen as referred to above and in WO 2007/134181.

In some embodiments, $R^{4*}$ and $R^{2*}$ together designate a biradical which comprise a substituted amino group in the bridge such as consist or comprise of the biradical —$CH_2$—N($R^c$)—, wherein $R^c$ is $C_{1-12}$alkyloxy. In some embodiments $R^{4*}$ and $R^{2*}$ together designate a biradical —$Cq_3q_4$-NOR—, wherein $q_3$ and $q_4$ are independently selected from the group consisting of hydrogen, halogen, $C_{1-6}$alkyl, substituted $C_{1-6}$alkyl, $C_{2-6}$alkenyl, substituted $C_{2-6}$alkenyl, $C_{2-6}$alkynyl or substituted $C_{2-6}$alkynyl, $C_{1-6}$alkoxyl, substituted $C_{1-6}$alkoxyl, acyl, substituted acyl, $C_{1-6}$ aminoalkyl or substituted $C_{1-6}$ aminoalkyl; wherein each substituted group is, independently, mono or poly substituted with substituent groups independently selected from halogen, $OJ_1$, $SJ_1$, $NJ_1J_2$, $COOJ_1$, CN, O—C(=O)$NJ_1J_2$, N(H)C(=NH)$NJ_1J_2$ or N(H)C(=X)=N(H)$J_2$ wherein X is O or S; and each of $J_1$ and $J_2$ is, independently, H, $C_{1-6}$alkyl, $C_{2-6}$alkenyl, $C_{2-6}$alkynyl, $C_{1-6}$ aminoalkyl or a protecting group. For all chiral centers, asymmetric groups may be found in either R or S orientation. Such bicyclic nucleotides are disclosed in WO2008/150729 which is hereby incorporated by reference in its entirety. In some embodiments, $R^{1*}$, $R^2$, $R^3$, $R^5$, $R^{5*}$ are independently selected from the group consisting of hydrogen, halogen, $C_{1-6}$alkyl, substituted $C_{1-6}$alkyl, $C_{2-6}$alkenyl, substituted $C_{2-6}$alkenyl, $C_{2-6}$alkynyl or substituted $C_{2-6}$alkynyl, $C_{1-6}$alkoxyl, substituted $C_{1-6}$alkoxyl, acyl, substituted acyl, $C_{1-6}$ aminoalkyl or substituted $C_{1-6}$ aminoalkyl. In some embodiments, $R^{1*}$, $R^2$, $R^3$, $R^5$, $R^{5*}$ are hydrogen. In some embodiments, $R^{1*}$, $R^2$, $R^3$ are hydrogen and one or both of $R^5$, $R^{5*}$ may be other than hydrogen as referred to above and in WO 2007/134181. In some embodiments $R^{4*}$ and $R^{2*}$ together designate a biradical (bivalent group) C($R^aR^b$)—O—, wherein $R^a$ and $R^b$ are each independently halogen, $C_1$-$C_{12}$alkyl, substituted $C_1$-$C_{12}$alkyl, $C_2$-$C_{12}$alkenyl, substituted $C_2$-$C_{12}$alkenyl, $C_2$-$C_{12}$alkynyl, substituted $C_2$-$C_{12}$alkynyl, $C_1$-$C_{12}$alkoxy, substituted $C_1$-$C_{12}$alkoxy, $OJ_1$, $SJ_1$, $SOJ_1$, $SO_2J_1$, $NJ_1J_2$, $N_3$, CN, C(=O)$OJ_1$, C(=O)$NJ_1J_2$, C(=O)$J_1$, O—C(=O)$NJ_1J_2$, N(H)C(=NH)$NJ_1J_2$, N(H)C(=O)$NJ_1J_2$ or N(H)C(=S)$NJ_1J_2$; or $R^a$ and $R^b$ together are =C(q3)(q4); $q_3$ and $q_4$ are each, independently, H, halogen, $C_1$-$C_{12}$alkyl or substituted $C_1$-$C_{12}$alkyl; each substituted group is, independently, mono or poly substituted with substituent groups independently selected from halogen, $C_1$-$C_6$-alkyl, substituted $C_1$-$C_6$alkyl, $C_2$-$C_6$alkenyl, substituted $C_2$-$C_6$-alkenyl, $C_2$-$C_6$alkynyl, substituted $C_2$-$C_6$alkynyl, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ or N(H)C(=S)$NJ_1J_2$; and each $J_1$ and $J_2$ is, independently, H, C1-$C_6$ alkyl, substituted C1-$C_6$ alkyl, $C_2$-$C_6$alkenyl, substituted $C_2$-$C_6$alkenyl, $C_2$-$C_6$alkynyl, substituted $C_2$-$C_6$alkynyl, C1-$C_6$ aminoalkyl, substituted C1-$C_6$ aminoalkyl or a protecting group. Such compounds are disclosed in WO2009006478A, hereby incorporated in its entirety by reference.

In some embodiments, $R^{4*}$ and $R^{2*}$ form the biradical —Q—, wherein Q is C($q_1$)($q_2$)C($q_3$)($q_4$), C($q_1$)=C($q_3$), C[=C($q_1$)($q_2$)]—C($q_3$)($q_4$) or C($q_1$)($q_2$)—[=C($q_3$)($q_4$)]; $q_1$, $q_2$, $q_3$, $q_4$ are each independently. H, halogen, $C_{1-12}$alkyl, substituted $C_{1-12}$alkyl, $C_{2-12}$alkenyl, substituted $C_{1-12}$alkoxy, $OJ_1$, $SJ_1$, $SOJ_1$, $SO_2J_1$, $NJ_1J_2$, $N_3$, CN, C(=O)$OJ_1$, C(=O)—$NJ_1J_2$, C(=O) $J_1$, —C(=O)$NJ_1J_2$, N(H)C(=NH)$NJ_1J_2$, N(H)C(=O)$NJ_1J_2$ or N(H)C(=S)$NJ_1J_2$; each $J_1$ and $J_2$ is, independently, H, $C_{1-6}$alkyl, $C_{2-6}$alkenyl, $C_{2-6}$alkynyl, $C_{1-6}$ aminoalkyl or a protecting group; and, optionally wherein when Q is C($q_1$)($q_2$)($q_3$)($q_4$) and one of $q_3$ or $q_4$ is $CH_3$ then at least one of the other of $q_3$ or $q_4$ or one of $q_1$ and $q_2$ is other than H. In some embodiments, $R^{1*}$, $R^2$, $R^3$, $R^5$, $R^{5*}$ are hydrogen. For all chiral centers, asymmetric groups may be found in either R or S orientation. Such bicyclic nucleotides are disclosed in WO2008/154401 which is hereby incorporated by reference in its entirety. In some embodiments, $R^{1*}$, $R^2$, $R^3$, $R^5$, $R^{5*}$ are independently selected from the group consisting of hydrogen, halogen, $C_{1-6}$alkyl, substituted $C_{1-6}$alkyl, $C_{2-6}$alkenyl, substituted $C_{2-6}$alkenyl, $C_{2-6}$alkynyl or substituted $C_{2-6}$alkynyl, $C_{1-6}$alkoxyl, substituted $C_{1-6}$alkoxyl, acyl, substituted acyl, $C_{1-6}$-aminoalkyl or substituted $C_{1-6}$ aminoalkyl. In some embodiments, $R^{1*}$, $R^2$, $R^3$, $R^5$, $R^{5*}$ are hydrogen. In some embodiments, $R^{1*}$, $R^2$, $R^3$ are hydrogen and one or both of $R^5$, $R^{5*}$ may be other than hydrogen as referred to above and in WO 2007/134181 or WO2009/067647 (alpha-L-bicyclic nucleic acids analogs).

In some embodiments the LNA used in the oligonucleotide compounds of the invention preferably has the structure of the general formula II:

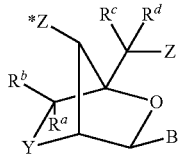

Formula II wherein Y is selected from the group consisting of —O—, —$CH_2$O—, —S—, —NH—, N($R^e$) and/or —$CH_2$—; Z and Z* are independently selected among an internucleotide linkage, $R^H$, a terminal group or a protecting group; B constitutes a natural or non-natural nucleotide base moiety (nucleobase), and $R^H$ is selected from hydrogen and $C_{1-4}$-alkyl; $R^a$, $R^b$ $R^c$, $R^d$ and $R^e$ are, optionally independently, selected from the group consisting of hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxycarbonyl, heteroaryloxy, heteroarylcarbonyl, amino, mono- and di($C_{1-6}$-alkyl) amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=$CH_2$); and $R^H$ is selected from hydrogen and $C_{1-4}$-alkyl. In some embodiments $R^a$, $R^b$ $R^c$, $R^d$ and $R^e$ are, optionally independently, selected from the group consisting of hydrogen and $C_{1-6}$alkyl, such as methyl. For all chiral centers, asymmetric groups may be found in either R or S orientation, for example, two exemplary stereochemical isomers include the beta-D and alpha-L isoforms, which may be illustrated as follows:

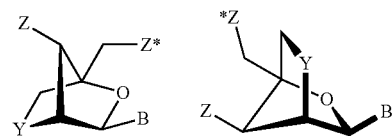

Specific exemplary LNA units are shown below:

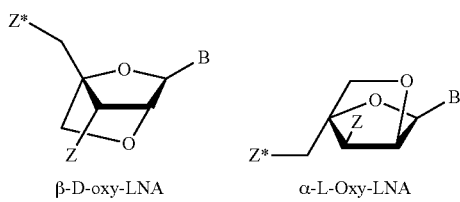

β-D-oxy-LNA          α-L-Oxy-LNA

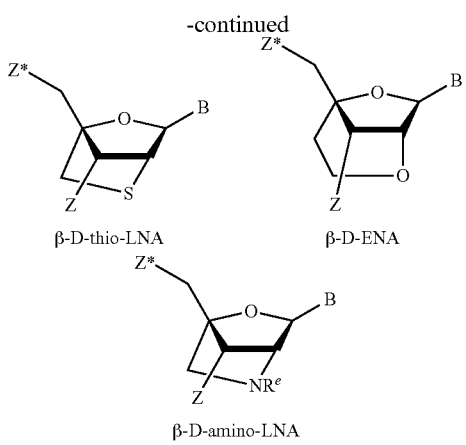

β-D-thio-LNA  β-D-ENA

β-D-amino-LNA

The term "thio-LNA" comprises a locked nucleotide in which Y in the general formula above is selected from S or —CH$_2$—S—. Thio-LNA can be in both beta-D and alpha-L-configuration.

The term "amino-LNA" comprises a locked nucleotide in which Y in the general formula above is selected from —N(H)—, N(R)—, CH$_2$—N(H)—, and —CH$_2$—N(R)— where R is selected from hydrogen and C$_{1-4}$-alkyl. Amino-LNA can be in both beta-D and alpha-L-configuration.

The term "oxy-LNA" comprises a locked nucleotide in which Y in the general formula above represents —O—. Oxy-LNA can be in both beta-D and alpha-L-configuration.

The term "ENA" comprises a locked nucleotide in which Y in the general formula above is —CH$_2$—O— (where the oxygen atom of —CH$_2$—O— is attached to the 2'-position relative to the base B). R$^e$ is hydrogen or methyl.

In some exemplary embodiments LNA is selected from beta-D-oxy-LNA, alpha-L-oxy-LNA, beta-D-amino-LNA and beta-D-thio-LNA, in particular beta-D-oxy-LNA.

RNAse Recruitment

It is recognised that an oligomeric compound may function via non RNase mediated degradation of target mRNA, such as by steric hindrance of translation, or other methods, however, the preferred oligomers of the invention are capable of recruiting an endoribonuclease (RNase), such as RNase H.

It is preferable that the oligomer, or contiguous nucleotide sequence, comprises of a region of at least 6, such as at least 7 consecutive nucleotide units, such as at least 8 or at least 9 consecutive nucleotide units (residues), including 7, 8, 9, 10, 11, 12, 13, 14, 15 or 16 consecutive nucleotides, which, when formed in a duplex with the complementary target RNA is capable of recruiting RNase. The contiguous sequence which is capable of recruiting RNAse may be region B as referred to in the context of a gapmer as described herein. In some embodiments the size of the contiguous sequence which is capable of recruiting RNAse, such as region B, may be higher, such as 10, 11, 12, 13, 14, 15, 16, 17, 18, 19 or 20 nucleotide units.

EP 1 222 309 provides in vitro methods for determining RNaseH activity, which may be used to determine the ability to recruit RNaseH. A oligomer is deemed capable of recruiting RNase H if, when provided with the complementary RNA target, it has an initial rate, as measured in pmol/l/min, of at least 1%, such as at least 5%, such as at least 10% or less than 20% of the equivalent DNA only oligonucleotide, with no 2' substitutions, with phosphorothioate linkage groups between all nucleotides in the oligonucleotide, using the methodology provided by Example 91-95 of EP 1 222 309.

In some embodiments, an oligomer is deemed essentially incapable of recruiting RNaseH if, when provided with the complementary RNA target, and RNaseH, the RNaseH initial rate, as measured in pmol/l/min, is less than 1%, such as less than 5%, such as less than 10% or less than 20% of the initial rate determined using the equivalent DNA only oligonucleotide, with no 2' substitutions, with phosphorothioate linkage groups between all nucleotides in the oligonucleotide, using the methodology provided by Example 91-95 of EP 1 222 309.

In other embodiments, an oligomer is deemed capable of recruiting RNaseH if, when provided with the complementary RNA target, and RNaseH, the RNaseH initial rate, as measured in pmol/l/min, is at least 20%, such as at least 40%, such as at least 60%, such as at least 80% of the initial rate determined using the equivalent DNA only oligonucleotide, with no 2' substitutions, with phosphorothioate linkage groups between all nucleotides in the oligonucleotide, using the methodology provided by Example 91-95 of EP 1 222 309.

Typically the region of the oligomer which forms the consecutive nucleotide units which, when formed in a duplex with the complementary target RNA is capable of recruiting RNase consists of nucleotide units which form a DNA/RNA like duplex with the RNA target—and include both DNA units and LNA units which are in the alpha-L configuration, particularly preferred being alpha-L-oxy LNA.

The oligomer of the invention may comprise a nucleotide sequence which comprises both nucleotides and nucleotide analogues, and may be in the form of a gapmer, a headmer or a mixmer.

A headmer is defined by a contiguous stretch of non-RNase recruiting nucleotide analogues at the 5'-end followed by a contiguous stretch of DNA or modified nucleotide units recognizable and cleavable by the RNase towards the 3'-end (such as at least 7 such nucleotides), and a tailmer is defined by a contiguous stretch of DNA or modified nucleotides recognizable and cleavable by the RNase at the 5'-end (such as at least 7 such nucleotides), followed by a contiguous stretch of non-RNase recruiting nucleotide analogues towards the 3'-end. Other chimeras according to the invention, called mixmers consisting of an alternate composition of DNA or modified nucleotides recognizable and cleavable by RNase and non-RNase recruiting nucleotide analogues. Some nucleotide analogues may also be able to mediate RNaseH binding and cleavage. Since α-L-LNA recruits RNaseH activity to a certain extent, smaller gaps of DNA or modified nucleotides recognizable and cleavable by the RNaseH for the gapmer construct might be required, and more flexibility in the mixmer construction might be introduced.

Gapmer Design

Preferably, the oligomer of the invention is a gapmer. A gapmer oligomer is an oligomer which comprises a contiguous stretch of nucleotides which is capable of recruiting an RNAse, such as RNAseH, such as a region of at least 6 or 7 DNA nucleotides, referred to herein in as region B, wherein region B is flanked both 5' and 3' by regions of affinity enhancing nucleotide analogues, such as between 1-6 nucleotide analogues 5' and 3' to the contiguous stretch of nucleotides which is capable of recruiting RNAse—these regions are referred to as regions A and C respectively.

In some embodiments, the nucleotides which are capable of recruiting RNAse are selected from the group consisting of DNA nucleotides, alpha-L-LNA nucleotides, C4' alkylayted DNA. (see PCT/EP2009/050349 hereby incorporated by reference), and UNA nucleotides (see Fluiter et al., Mol. Biosyst., 2009, 10, 1039 hereby incorporated by reference). In some embodiments, region B consists of a contiguous length of at least 6 or 7 DNA nucleotides, or nucleotides selected from the group consisting of DNA and alpha-L-LNA.

Preferably the gapmer comprises a (poly)nucleotide sequence of formula (5' to 3'), A-B-C, or optionally A-B-C-D or D-A-B-C, wherein; region A (5' region) consists or comprises of at least one nucleotide analogue, such as at least one LNA unit, such as between 1-6 nucleotide analogues, such as LNA units, and; region B consists or comprises of at least five consecutive nucleotides which are capable of recruiting RNAse (when formed in a duplex with a complementary RNA molecule, such as the mRNA target), such as DNA nucleotides, and; region C (3'region) consists or comprises of at least one nucleotide analogue, such as at least one LNA unit, such as between 1-6 nucleotide analogues, such as LNA units, and; region D, when present consists or comprises of 1, 2 or 3 nucleotide units, such as DNA nucleotides.

In some embodiments, region A consists of 1, 2, 3, 4, 5 or 6 nucleotide analogues, such as LNA units, such as between 2-5 nucleotide analogues, such as 2-5 LNA units, such as 3 or 4 nucleotide analogues, such as 3 or 4 LNA units; and/or region C consists of 1, 2, 3, 4, 5 or 6 nucleotide analogues, such as LNA units, such as between 2-5 nucleotide analogues, such as 2-5 LNA units, such as 3 or 4 nucleotide analogues, such as 3 or 4 LNA units.

In some embodiments B consists or comprises of 5, 6, 7, 8, 9, 10, 11 or 12 consecutive nucleotides which are capable of recruiting RNAse, or between 6-10, or between 7-9, such as 8 consecutive nucleotides which are capable of recruiting RNAse. In some embodiments region B consists or comprises at least one DNA nucleotide unit, such as 1-12 DNA units, preferably between 4-12 DNA units, more preferably between 6-10 DNA units, such as between 7-10 DNA units, most preferably 8, 9 or 10 DNA units.

In some embodiments region A consist of 3 or 4 nucleotide analogues, such as LNA, region B consists of 7, 8, 9 or 10 DNA units, and region C consists of 3 or 4 nucleotide analogues, such as LNA. Such designs include (A-B-C) 3-10-3, 3-10-4, 4-10-3, 3-9-3, 3-9-4, 4-9-3, 3-8-3, 3-8-4, 4-8-3, 3-7-3, 3-7-4, 4-7-3, and may further include region D, which may have one or 2 nucleotide units, such as DNA units.

Further gapmer designs are disclosed in WO2004/046160 and are hereby incorporated by reference.

U.S. provisional application, 60/977409, hereby incorporated by reference, refers to 'shortmer gapmer' oligomers, which, in some embodiments may be the gapmer oligomer according to the present invention.

In some embodiments the oligomer is consisting of a contiguous nucleotide sequence of a total of 10, 11, 12, 13 or 14 nucleotide units, wherein the contiguous nucleotide sequence is of formula (5'-3'), A-B-C, or optionally A-B-C-D or D-A-B-C, wherein; A consists of 1, 2 or 3 nucleotide analogue units, such as LNA units; B consists of 7, 8 or 9 contiguous nucleotide units which are capable of recruiting RNAse when formed in a duplex with a complementary RNA molecule (such as a mRNA target); and C consists of 1, 2 or 3 nucleotide analogue units, such as LNA units. When present, D consists of a single DNA unit.

In some embodiments A consists of 1 LNA unit. In some embodiments A consists of 2 LNA units. In some embodiments A consists of 3 LNA units. In some embodiments C consists of 1 LNA unit. In some embodiments C consists of 2 LNA units. In some embodiments C consists of 3 LNA units. In some embodiments B consists of 7 nucleotide units. In some embodiments B consists of 8 nucleotide units. In some embodiments B consists of 9 nucleotide units. In some embodiments B comprises of between 1-9 DNA units, such as 2, 3, 4, 5, 6, 7 or 8 DNA units. In some embodiments B consists of DNA units. In some embodiments B comprises of at least one LNA unit which is in the alpha-L configuration, such as 2, 3, 4, 5, 6, 7, 8 or 9 LNA units in the alpha-L-configuration. In some embodiments B comprises of at least one alpha-L-oxy LNA unit or wherein all the LNA units in the alpha-L-configuration are alpha-L-oxy LNA units. In some embodiments the number of nucleotides present in A-B-C are selected from the group consisting of (nucleotide analogue units—region B—nucleotide analogue units): 1-8-1, 1-8-2, 2-8-1, 2-8-2, 3-8-3, 2-8-3, 3-8-2, 4-8-1, 4-8-2, 1-8-4, 2-8-4, or 1-9-1, 1-9-2, 2-9-1, 2-9-2, 2-9-3, 3-9-2, 1-9-3, 3-9-1, 4-9-1, 1-9-4, or; 1-10-1, 1-10-2, 2-10-1, 2-10-2, 1-10-3, 3-10-1. In some embodiments the number of nucleotides in A-B-C are selected from the group consisting of: 2-7-1, 1-7-2, 2-7-2, 3-7-3, 2-7-3, 3-7-2, 3-7-4, and 4-7-3. In some embodiments both A and C consists of two LNA units each, and B consists of 8 or 9 nucleotide units, preferably DNA units.

Internucleotide Linkages

The terms "linkage group" or "internucleotide linkage" are intended to mean a group capable of covalently coupling together two nucleotides, two nucleotide analogues, and a nucleotide and a nucleotide analogue, etc. Specific and preferred examples include phosphate groups and phosphorothioate groups.

The nucleotides of the oligomer of the invention or contiguous nucleotides sequence thereof are coupled together via linkage groups. Suitably each nucleotide is linked to the 3' adjacent nucleotide via a linkage group.

Suitable internucleotide linkages include those listed within PCT/DK2006/000512, for example the internucleotide linkages listed on the first paragraph of page 34 of PCT/DK2006/000512 (hereby incorporated by reference).

It is, in some embodiments, preferred to modify the internucleotide linkage from its normal phosphodiester to one that is more resistant to nuclease attack, such as phosphorothioate or boranophosphate—these two, being cleavable by RNase H, also allow that route of antisense inhibition in reducing the expression of the target gene.

Suitable sulphur (S) containing internucleotide linkages as provided herein may be preferred. Phosphorothioate internucleotide linkages are also preferred, particularly for the gap region (B) of gapmers. Phosphorothioate linkages may also be used for the flanking regions (A and C, and for linking A or C to D, and within region D, as appropriate).

Regions A, B and C, may however comprise internucleotide linkages other than phosphorothioate, such as phosphodiester linkages, particularly, for instance when the use of nucleotide analogues protects the internucleotide linkages within regions A and C from endo-nuclease degradation—such as when regions A and C comprise LNA nucleotides.

The internucleotide linkages in the oligomer may be phosphodiester, phosphorothioate or boranophosphate so as to allow RNase H cleavage of targeted RNA. Phosphorothioate is preferred, for improved nuclease resistance and other reasons, such as ease of manufacture.

In one aspect of the oligomer of the invention, the nucleotides and/or nucleotide analogues are linked to each other by means of phosphorothioate groups.

It is recognised that the inclusion of phosphodiester linkages, such as one or two linkages, into an otherwise phosphorothioate oligomer, particularly between or adjacent to nucleotide analogue units (typically in region A and or C) can modify the bioavailability and/or bio-distribution of an oligomer—see WO2008/053314, hereby incorporated by reference.

In some embodiments, such as the embodiments referred to above, where suitable and not specifically indicated, all remaining linkage groups are either phosphodiester or phosphorothioate, or a mixture thereof.

In some embodiments all the internucleotide linkage groups are phosphorothioate.

When referring to specific gapmer oligonucleotide sequences, such as those provided herein it will be understood that, in various embodiments, when the linkages are phosphorothioate linkages, alternative linkages, such as those disclosed herein may be used, for example phosphate (phosphodiester) linkages may be used, particularly for linkages between nucleotide analogues, such as LNA, units. Likewise, when referring to specific gapmer oligonucleotide sequences, such as those provided herein, when the C residues are annotated as 5'methyl modified cytosine, in various embodiments, one or more of the Cs present in the oligomer may be unmodified C residues. in some embodiments in some embodiments Oligomeric Compounds The oligomers of the invention may, for example, be selected from the group consisting of: SEQ ID NOs: 26-50. In a specially preferred embodiment, the oligomers of the invention are selected from the group consisting of SEQ ID NOs: 28, 29, 44 and 45.

Conjugates

In the context the term "conjugate" is intended to indicate a heterogenous molecule formed by the covalent attachment ("conjugation") of the oligomer as described herein to one or more non-nucleotide, or non-polynucleotide moieties. Examples of non-nucleotide or non-polynucleotide moieties include macromolecular agents such as proteins, fatty acid chains, sugar residues, glycoproteins, polymers, or combinations thereof. Typically proteins may be antibodies for a target protein. Typical polymers may be polyethylene glycol.

of a specified nucleic acid or nucleotide sequence, as herein disclosed, the compound may also comprise at least one non-nucleotide or non-polynucleotide moiety (e.g. not comprising one or more nucleotides or nucleotide analogues) covalently attached to said compound.

Conjugation (to a conjugate moiety) may enhance the activity, cellular distribution or cellular uptake of the oligomer of the invention. Such moieties include, but are not limited to, antibodies, polypeptides, lipid moieties such as a cholesterol moiety, cholic acid, a thioether, e.g. Hexyl-s-tritylthiol, a thiocholesterol, an aliphatic chain, e.g., dodecandiol or undecyl residues, a phospholipids, e.g., di-hexadecyl-rac-glycerol or triethylammonium 1,2-di-o-hexadecyl-rac-glycero-3-h-phosphonate, a polyamine or a polyethylene glycol chain, an adamantane acetic acid, a palmityl moiety, an octadecylamine or hexylamino-carbonyl-oxycholesterol moiety.

The oligomers of the invention may also be conjugated to active drug substances, for example, aspirin, ibuprofen, a sulfa drug, an antidiabetic, an antibacterial or an antibiotic.

In certain embodiments the conjugated moiety is a sterol, such as cholesterol.

In various embodiments, the conjugated moiety comprises or consists of a positively charged polymer, such as a positively charged peptides of, for example between 1-50, such as 2-20 such as 3-10 amino acid residues in length, and/or polyalkylene oxide such as polyethylglycol(PEG) or polypropylene glycol—see WO 2008/034123, hereby incorporated by reference. Suitably the positively charged polymer, such as a polyalkylene oxide may be attached to the oligomer of the invention via a linker such as the releasable inker described in WO 2008/034123.

By way of example, the following conjugate moieties may be used in the conjugates of the invention:

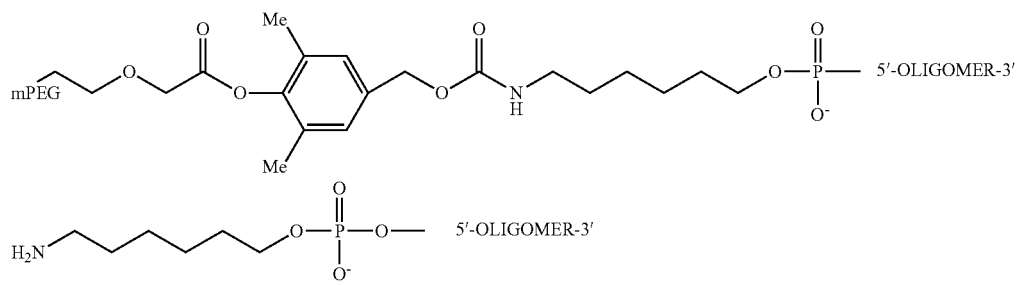

Therefore, in various embodiments, the oligomer of the invention may comprise both a polynucleotide region which typically consists of a contiguous sequence of nucleotides, and a further non-nucleotide region. When referring to the oligomer of the invention consisting of a contiguous nucleotide sequence, the compound may comprise non-nucleotide components, such as a conjugate component.

In various embodiments of the invention the oligomeric compound is linked to ligands/conjugates, which may be used, e.g. to increase the cellular uptake of oligomeric compounds. WO2007/031091 provides suitable ligands and conjugates, which are hereby incorporated by reference.

The invention also provides for a conjugate comprising the compound according to the invention as herein described, and at least one non-nucleotide or non-polynucleotide moiety covalently attached to said compound. Therefore, in various embodiments where the compound of the invention consists Activated Oligomers The term "activated oligomer," as used herein, refers to an oligomer of the invention that is covalently linked (i.e., functionalized) to at least one functional moiety that permits covalent linkage of the oligomer to one or more conjugated moieties, i.e., moieties that are not themselves nucleic acids or monomers, to form the conjugates herein described. Typically, a functional moiety will comprise a chemical group that is capable of covalently bonding to the oligomer via, e.g., a 3'-hydroxyl group or the exocyclic $NH_2$ group of the adenine base, a spacer that is preferably hydrophilic and a terminal group that is capable of binding to a conjugated moiety (e.g., an amino, sulfhydryl or hydroxyl group). In some embodiments, this terminal group is not protected, e.g., is an $NH_2$ group. In other embodiments, the terminal group is protected, for example, by any suitable protecting group such as those described in "Protective Groups in Organic Synthesis" by Theodora W Greene and Peter G M Wuts, 3rd edition (John Wiley & Sons, 1999). Examples of suitable hydroxyl protecting groups include esters such as acetate ester, aralkyl groups such as benzyl, diphenylmethyl, or triphenylmethyl, and tetrahydropyranyl. Examples of suitable amino protecting groups include benzyl, alpha-methylbenzyl, diphenylmethyl, triphenylmethyl, benzyloxycarbonyl, tert-butoxycarbonyl, and acyl groups such as trichloroacetyl or trifluoroacetyl. In some embodiments, the functional moiety is self-cleaving. In other embodiments, the functional moiety is biodegradable. See e.g., U.S. Pat. No. 7,087,229, which is incorporated by reference herein in its entirety.

In some embodiments, oligomers of the invention are functionalized at the 5' end in order to allow covalent attachment of the conjugated moiety to the 5' end of the oligomer. In other embodiments, oligomers of the invention can be functionalized at the 3' end. In still other embodiments, oligomers of the invention can be functionalized along the backbone or on the heterocyclic base moiety. In yet other embodiments, oligomers of the invention can be functionalized at more than one position independently selected from the 5' end, the 3' end, the backbone and the base.

In some embodiments, activated oligomers of the invention are synthesized by incorporating during the synthesis one or more monomers that is covalently attached to a functional moiety. In other embodiments, activated oligomers of the invention are synthesized with monomers that have not been functionalized, and the oligomer is functionalized upon completion of synthesis. In some embodiments, the oligomers are functionalized with a hindered ester containing an aminoalkyl linker, wherein the alkyl portion has the formula $(CH_2)_w$, wherein w is an integer ranging from 1 to 10, preferably about 6, wherein the alkyl portion of the alkylamino group can be straight chain or branched chain, and wherein the functional group is attached to the oligomer via an ester group (—O—C(O)—$(CH_2)_w$NH).

In other embodiments, the oligomers are functionalized with a hindered ester containing a $(CH_2)_w$-sulfhydryl (SH) linker, wherein w is an integer ranging from 1 to 10, preferably about 6, wherein the alkyl portion of the alkylamino group can be straight chain or branched chain, and wherein the functional group attached to the oligomer via an ester group (—O—C(O)—$(CH_2)_w$SH)

In some embodiments, sulfhydryl-activated oligonucleotides are conjugated with polymer moieties such as polyethylene glycol or peptides (via formation of a disulfide bond).

Activated oligomers containing hindered esters as described above can be synthesized by any method known in the art, and in particular by methods disclosed in PCT Publication No. WO 2008/034122 and the examples therein, which is incorporated herein by reference in its entirety.

In still other embodiments, the oligomers of the invention are functionalized by introducing sulfhydryl, amino or hydroxyl groups into the oligomer by means of a functionalizing reagent substantially as described in U.S. Pat. Nos. 4,962,029 and 4,914,210, i.e., a substantially linear reagent having a phosphoramidite at one end linked through a hydrophilic spacer chain to the opposing end which comprises a protected or unprotected sulfhydryl, amino or hydroxyl group. Such reagents primarily react with hydroxyl groups of the oligomer. In some embodiments, such activated oligomers have a functionalizing reagent coupled to a 5'-hydroxyl group of the oligomer. In other embodiments, the activated oligomers have a functionalizing reagent coupled to a 3'-hydroxyl group. In still other embodiments, the activated oligomers of the invention have a functionalizing reagent coupled to a hydroxyl group on the backbone of the oligomer. In yet further embodiments, the oligomer of the invention is functionalized with more than one of the functionalizing reagents as described in U.S. Pat. Nos. 4,962,029 and 4,914,210, incorporated herein by reference in their entirety. Methods of synthesizing such functionalizing reagents and incorporating them into monomers or oligomers are disclosed in U.S. Pat. Nos. 4,962,029 and 4,914,210.

In some embodiments, the 5'-terminus of a solid-phase bound oligomer is functionalized with a dienyl phosphoramidite derivative, followed by conjugation of the deprotected oligomer with, e.g., an amino acid or peptide via a Diels-Alder cycloaddition reaction.

In various embodiments, the incorporation of monomers containing 2'-sugar modifications, such as a 2'-carbamate substituted sugar or a 2'-(O-pentyl-N-phthalimido)-deoxyribose sugar into the oligomer facilitates covalent attachment of conjugated moieties to the sugars of the oligomer. In other embodiments, an oligomer with an amino-containing linker at the 2'-position of one or more monomers is prepared using a reagent such as, for example, 5'-dimethoxytrityl-2'-O-(e-phthalimidylaminopentyl)-2'-deoxyadenosine-3'-N,N-diisopropyl-cyanoethoxy phosphoramidite. See, e.g., Manoharan, et al., Tetrahedron Letters, 1991, 34, 7171.

In still further embodiments, the oligomers of the invention may have amine-containing functional moieties on the nucleobase, including on the N6 purine amino groups, on the exocyclic N2 of guanine, or on the N4 or 5 positions of cytosine. In various embodiments, such functionalization may be achieved by using a commercial reagent that is already functionalized in the oligomer synthesis.

Some functional moieties are commercially available, for example, heterobifunctional and homobifunctional linking moieties are available from the Pierce Co. (Rockford, Ill.). Other commercially available linking groups are 5'-Amino-Modifier C6 and 3'-Amino-Modifier reagents, both available from Glen Research Corporation (Sterling, Va.). 5'-Amino-Modifier C6 is also available from ABI (Applied Biosystems Inc., Foster City, Calif.) as Aminolink-2, and 3'-Amino-Modifier is also available from Clontech Laboratories Inc. (Palo Alto, Calif.).

Compositions

The oligomer of the invention may be used in pharmaceutical formulations and compositions. Suitably, such compositions comprise a pharmaceutically acceptable diluent, carrier, salt or adjuvant. PCT/DK2006/000512 provides suitable and preferred pharmaceutically acceptable diluents, carrier and adjuvants—which are hereby incorporated by reference. Suitable dosages, formulations, administration routes, compositions, dosage forms, combinations with other therapeutic agents, pro-drug formulations are also provided in PCT/DK2006/000512—which are also hereby incorporated by reference.

Applications

The oligomers of the invention may be utilized as research reagents for, for example, diagnostics, therapeutics and prophylaxis.

In research, such oligomers may be used to specifically inhibit the synthesis of APO-B100 protein (typically by degrading or inhibiting the mRNA and thereby prevent protein formation) in cells and experimental animals thereby facilitating functional analysis of the target or an appraisal of its usefulness as a target for therapeutic intervention.

In diagnostics the oligomers may be used to detect and quantitate APO-B100 expression in cell and tissues by northern blotting, in-situ hybridisation or similar techniques.

For therapeutics, an animal or a human, suspected of having a disease or disorder, which can be treated by modulating the expression of APO-B100 is treated by administering oligomeric compounds in accordance with this invention. Further provided are methods of treating a mammal, such as treating a human, suspected of having or being prone to a disease or condition, associated with expression of APO-B100 by administering a therapeutically or prophylactically effective amount of one or more of the oligomers or compositions of the invention. The oligomer, a conjugate or a pharmaceutical composition according to the invention is typically administered in an effective amount.

The invention also provides for the use of the compound or conjugate of the invention as described for the manufacture of a medicament for the treatment of a disorder as referred to herein, or for a method of the treatment of as a disorder as referred to herein.

The invention also provides for a method for treating a disorder as referred to herein said method comprising administering a compound according to the invention as herein described, and/or a conjugate according to the invention, and/or a pharmaceutical composition according to the invention to a patient in need thereof.

Medical Indications

The oligomers and other compositions according to the invention can be used for the treatment of conditions associated with over expression or expression of mutated version of the APO-B100.

The invention further provides use of a compound of the invention in the manufacture of a medicament for the treatment of a disease, disorder or condition as referred to herein.

Generally stated, one aspect of the invention is directed to a method of treating a mammal suffering from or susceptible to conditions associated with abnormal levels of APO-B100, comprising administering to the mammal an therapeutically effective amount of an oligomer targeted to APO-B100 that comprises one or more LNA units. The oligomer, a conjugate or a pharmaceutical composition according to the invention is typically administered in an effective amount.

The disease or disorder, as referred to herein, may, In some embodiments be associated with a mutation in the APO-B100 gene or a gene whose protein product is associated with or interacts with APO-B100. Therefore, in some embodiments, the target mRNA is a mutated form of the APO-B100 sequence.

An interesting aspect of the invention is directed to the use of an oligomer (compound) as defined herein or a conjugate as defined herein for the preparation of a medicament for the treatment of a disease, disorder or condition as referred to herein.

The methods of the invention are preferably employed for treatment or prophylaxis against diseases caused by abnormal levels of APO-B100.

Alternatively stated, In some embodiments, the invention is furthermore directed to a method for treating abnormal levels of APO-B100, said method comprising administering a oligomer of the invention, or a conjugate of the invention or a pharmaceutical composition of the invention to a patient in need thereof.

The invention also relates to an oligomer, a composition or a conjugate as defined herein for use as a medicament.

The invention further relates to use of a compound, composition, or a conjugate as defined herein for the manufacture of a medicament for the treatment of abnormal levels of APO-B100 or expression of mutant forms of APO-B100 (such as allelic variants, such as those associated with one of the diseases referred to herein).

Moreover, the invention relates to a method of treating a subject suffering from a disease or condition such as those referred to herein.

A patient who is in need of treatment is a patient suffering from or likely to suffer from the disease or disorder.

In some embodiments, the term 'treatment' as used herein refers to both treatment of an existing disease (e.g. a disease or disorder as herein referred to), or prevention of a disease, i.e. prophylaxis. It will therefore be recognised that treatment as referred to herein may, in some embodiments, be prophylactic.

EMBODIMENTS

The following embodiments of the present invention may be used in combination with the other embodiments described herein.

1. An oligomer of between 10-30 nucleotides in length which comprises a contiguous nucleotide sequence of a total of between 10-30 nucleotides, wherein said contiguous nucleotide sequence is at least 80% homologous to a region corresponding to a mammalian APO-B100 gene or the reverse complement of an mRNA, such as human APO-B100 mRNA or naturally occurring variant thereof, and wherein the contiguous nucleotide sequence is at least 80% homologous to a region corresponding to any of SEQ ID NO: 1-25.

2. The oligomer according to embodiment 1, wherein the contiguous nucleotide sequence comprises no mismatches or no more than one or two mismatches with the reverse complement of the corresponding region of human APO-B100 mRNA.

3. The oligomer according to any one of embodiments 1-2, wherein the nucleotide sequence of the oligomer consists of the contiguous nucleotide sequence.

4. The oligomer according to any one of embodiments 1-3, wherein the contiguous nucleotide sequence is between 10-18 nucleotides in length.

5. The oligomer according to any one of embodiments 1-4, wherein the contiguous nucleotide sequence comprises nucleotide analogues.

6. The oligomer according to embodiment 5, wherein the nucleotide analogues are sugar modified nucleotides, such as sugar modified nucleotides selected from the group consisting of: Locked Nucleic Acid (LNA) units; 2'-O-alkyl-RNA units, 2'-OMe-RNA units, 2'-amino-DNA units, and 2'-fluoro-DNA units.

7. The oligomer according to embodiment 5, wherein the nucleotide analogues are LNA.

8. The oligomer according to any one of embodiment 5-7 which is a gapmer.

9. The oligomer according to any one of embodiments 1-9, wherein the oligomer consists of or comprises any one of SEQ ID NO's: 26-50

10. The oligomer according to any one of embodiments 1-9, wherein the oligomer consists of or comprises any one of SEQ ID NO's: 28, 29, 44 or 45.

11. The oligomer according to any one of embodiments 1-10, which inhibits the expression of APO-B100 gene or mRNA in a cell which is expressing APO-B100 gene or mRNA.

12. A conjugate comprising the oligomer according to any one of embodiments 1-11, and at least one non-nucleotide or non-polynucleotide moiety covalently attached to said oligomer.

13. A pharmaceutical composition comprising the oligomer according to any one of embodiments 1-11, or the conjugate according to claim 12, and a pharmaceutically acceptable diluent, carrier, salt or adjuvant.

14. The oligomer according to any one of embodiments 1-11, or the conjugate according to embodiment 12, for use as a medicament, such as for the treatment of diseases associated with apolipoproteinB activity, such as in non-limiting example, different types of HDL/LDL cholesterol imbalance; dyslipidemias, e.g., familial combined hyperlipidemia (FCHL), acquired hyperlipidemia, hypercholesterolemia, statin-resistant hypercholesterolemia; coronary artery disease (CAD), coronary heart disease (CHD), atherosclerosis.

15. The use of an oligomer according to any one of the embodiments 1-11, or a conjugate as defined in claim 12, for the manufacture of a medicament for the treatment of diseases associated with apolipoproteinB activity, such as in non-limiting example, different types of HDL/LDL cholesterol imbalance; dyslipidemias, e.g., familial combined hyperlipidemia (FCHL), acquired hyperlipidemia, hypercholesterolemia, statin-resistant hypercholesterolemia; coronary artery disease (CAD), coronary heart disease (CHD), atherosclerosis.

16. A method of treating diseases associated with apolipoproteinB activity, such as in non-limiting example, different types of HDL/LDL cholesterol imbalance; dyslipidemias, e.g., familial combined hyperlipidemia (FCHL), acquired hyperlipidemia, hypercholesterolemia, statin-resistant hypercholesterolemia; coronary artery disease (CAD), coronary heart disease (CHD), atherosclerosis, said method comprising administering an effective amount of an oligomer according to any one of the embodiments 1-11, or a conjugate according to embodiment 12, or a pharmaceutical composition according to claim 13, to a patient suffering from, or likely to suffer from diseases associated with apolipoproteinB activity, such as in non-limiting example, different types of HDL/LDL cholesterol imbalance; dyslipidemias, e.g., familial combined hyperlipidemia (FCHL), acquired hyperlipidemia, hypercholesterolemia, statin-resistant hypercholesterolemia; coronary artery disease (CAD), coronary heart disease (CHD), atherosclerosis.

17. A method for the inhibition of APO-B100 in a cell which is expressing APO-B100, said method comprising administering an oligomer according to any one of the embodiments 1-11, or a conjugate according to embodiment 12 to said cell so as to inhibit APO-B100 in said cell.

18. In one embodiment, according to any one of embodiments 1-17, one or more of the oxy LNA nucleotide analogues in the compounds of SEQ ID NO: 26-50 are replaced with another LNA than oxy LNA.

19. In one embodiment according to embodiment 18, the LNA is selected from 2'O-methoxyethyl bicyclic nucleic acid, 2'O-ethyl bicyclic nucleic acid, ENA, beta-D-amino-LNA and beta-D-thio-LNA.

EXAMPLES

Example 1

Monomer Synthesis

The LNA monomer building blocks and derivatives thereof were prepeared using standard methods, such as the published procedures and references cited in WO2007/031081.

Example 2

Oligonucleotide Synthesis

Oligonucleotides were synthesized using the method described in example 2 in WO2007/031081, which is hereby incorporated by reference.

TABLE 2

Oligonucleotide compounds of the invention

| Test substance | Length | Target seq |
|---|---|---|
| SEQ ID NO: 1 | 14 | 5'-TCTGAAGTCCATGA-3' |
| SEQ ID NO: 2 | 14 | 5'-GGATCAAATATAAG-3' |
| SEQ ID NO: 3 | 14 | 5'-GTTGACACTGTCTG-3' |
| SEQ ID NO: 4 | 12 | 5'-GTTGACACTGTC-3' |
| SEQ ID NO: 5 | 14 | 5'-GACTGCCTGTTCTC-3' |
| SEQ ID NO: 6 | 13 | 5'-CGTTGGAGTAAGC-3' |
| SEQ ID NO: 7 | 14 | 5'-GCGTTGGAGTAAGC-3' |
| SEQ ID NO: 8 | 14 | 5'-CTCTGTGATCCAGG-3' |
| SEQ ID NO: 9 | 14 | 5'-GGACTCTGTGATCC-3' |
| SEQ ID NO: 10 | 14 | 5'-CTGTTTGAGGGACT-3' |
| SEQ ID NO: 11 | 14 | 5'-GAGATGGCAGATGG-3' |
| SEQ ID NO: 12 | 14 | 5'-GCTGGTGTTGCCAC-3' |
| SEQ ID NO: 13 | 13 | 5'-CAGATCCTTGCAC-3' |
| SEQ ID NO: 14 | 14 | 5'-CCAGATCCTTGCAC-3' |
| SEQ ID NO: 15 | 12 | 5'-ACCTTTTGAGAC-3' |
| SEQ ID NO: 16 | 14 | 5'-CAATGTTCAGACTG-3' |
| SEQ ID NO: 17 | 14 | 5'-CCTGCAATGTTCAG-3' |

TABLE 2-continued

Oligonucleotide compounds of the invention

Test substance  Length  Target seq

SEQ ID NO: 18    14    5'-TAGGGCTGTAGCTG-3'

SEQ ID NO: 19    14    5'-GTTGGTCTACTTCA-3'

SEQ ID NO: 20    14    5'-CCAACCAATTTCTC-3'

SEQ ID NO: 21    14    5'-GTCAATTGTAAAGG-3'

SEQ ID NO: 22    14    5'-GTTTAAGAAATCCA-3'

SEQ ID NO: 23    12    5'-CTTAGTGTTAGC-3'

SEQ ID NO: 24    12    5'-GGTTCTTAGTGT-3'

SEQ ID NO: 25    14    5'-CTGGTTCTTAGTGT-3'

SEQ ID NO: 26          5'-TsomCsoTsogsasasgstscscsasTsoGsoAo-3'

SEQ ID NO: 27          5'-GsoGsoAsotscsasasastsastsAsoAsoG o-3'

SEQ ID NO: 28          5'-GsoTsoTsogsascsascstsgstsmCsoTsoGo-3'

SEQ ID NO: 29          5'-GsoTsotsgsascsascstsgsTsomC o-3'

SEQ ID NO: 30          5'-GsoAsomCsotsgscscstsgststsmCsoTsomCo-3'

SEQ ID NO: 31          5'-mCsoGsoTsotsgsgsasgstsasasGsomC o-3'

SEQ ID NO: 32          5'-GsomCsoGsotststsgsgsasgstsasAsoGsomC o-3'

SEQ ID NO: 33          5'-mCsoTsomCsotsgtsgsastscscsAsoGsoG o-3'

SEQ ID NO: 34          5'-GsoGsoAsocstscstsgstsgsasTsomCsomCo-3'

SEQ ID NO: 35          5'-mCsoTsoGsotstsgsasgsgsgsAsomCsoT o-3'

SEQ ID NO: 36          5'-GsoAsoGsoastsgsgscsasgsasTsoGsoG o-3'

SEQ ID NO: 37          5'-GsomCsoTsogsgstsgststsgscsmCsoAsomCo-3'

SEQ ID NO: 38          5'-mCsoAsoGsoastscscststsgscsAsomC o-3'

SEQ ID NO: 39          5'-mCsomCsoAsogsastscscststsgsmCsoAsomCo-3'

SEQ ID NO: 40          5'-AsomCso cstststststsgsasgsAsomC o-3'

SEQ ID NO: 41          5'-mCsoAsoAsotsgststscsasgsasmCsoTsoG o-3'

SEQ ID NO: 42          5'-mCsomCsoTsogscsasastsgststsmCsoAsoG o-3'

SEQ ID NO: 43          5'-TsoAsoGsogsgscstsgstsasgsmCsoTsoG o-3'

SEQ ID NO: 44          5'-GsoTsoTsogsgstscstsascstsTsomCsoA o-3'

SEQ ID NO: 45          5'-mCsomCsoAsoascscsasas tststsmCsoTsomCo-3'

SEQ ID NO: 46          5'-GsoTsomCsoasastststsgstsasasAsoGsoG o-3'

SEQ ID NO: 47          5'-GsoTsoTsotsasasgsasasastsmCsomCsoA o-3'

SEQ ID NO: 48          5'-mCsoTsotsasgstsgststsasGsomC o-3'

SEQ ID NO: 49          5'-GsoGso tstscststsasgstsGsoT o-3'

SEQ ID NO: 50          5'-mCsoTsoGsogststscststsasgsTsoGsoT o-3'

SEQ ID NO: 51          5'-GsomCsoaststsgsgstsasstsTsomCsoAo-3'

In SEQ ID NOs: 26-51, upper case letters indicates nucleotide analogue units (LNA), superscript letter "o" indicates oxy-LNA, "m" indicates methyl C-LNA and the subscript letter "s" represents phosphorothioate linkage. Absence of "s" indicates phosphodiester linkage.

Example 3

Assays

Antisense modulation of apoB-100 expression can be assayed in a variety of ways known in the art. For example, apoB-100 mRNA levels can be quantified by, e.g. Northern blot analysis, competitive polymerase chain reaction (PCR), or real-time PCR. Real-time quantitative PCR is presently preferred. RNA analysis can be performed on total cellular RNA or mRNA. Methods of RNA isolation and RNA analysis such as Northern blot analysis are routine in the art and is taught in, for example, Current Protocols in Molecular Biology, John Wiley and Sons.

Real-time quantitative (PCR) can be conveniently accomplished using the commercially iQ Multi-Color Real Time PCR Detection System available from BioRAD. Real-time Quantitative PCR is a technique well known in the art and is taught in for example Heid et al. Real time quantitative PCR, Genome Research (1996), 6: 986-994.

Example 4

In Vitro Model: Cell Culture

The effect of antisense compounds on target nucleic acid expression can be tested in any of a variety of cell types provided that the target nucleic acid is present at measurable levels. Target can be expressed endogenously or by transient or stable transfection of a nucleic acid encoding said nucleic acid.

The expression level of target nucleic acid can be routinely determined using, for example, Northern blot analysis, Quantitative PCR, Ribonuclease protection assays. The following cell types are provided for illustrative purposes, but other cell types can be routinely used, provided that the target is expressed in the cell type chosen.

Cells were cultured in the appropriate medium as described below and maintained at 37° C. at 95-98% humidity and 5% $CO_2$. Cells were routinely passaged 2-3 times weekly.

BNCL-2: Mouse liver cell line BNCL-2 was purchased from ATCC and cultured in DMEM (Sigma) with 10% FBS+ Glutamax I+non-essential amino acids+gentamicin.

Hepa1-6: Mouse liver cell line Hepa1-6 was purchased from ATCC and cultured in DMEM (Sigma) with 10% FBS+ Glutamax I+non-essential amino acids+gentamicin.

HepG2: Human liver cell line HepG2 was purchased from ATCC and cultured in Eagle MEM (Sigma) with 10% FBS+ Glutamax I+non-essential amino acids+gentamicin.

HuH-7: Human liver cell line HepG2 was purchased from ATCC and cultured in Eagle MEM (Sigma) with 10% FBS+ Glutamax I+non-essential amino acids+gentamicin.

Example 5

In Vitro Model: Treatment with Antisense Oligonucleotide

Cell culturing and transfections: Huh-7 and Hepa 1-6 cells were seeded in 6-well plates at 37° C. (5% $CO_2$) in growth media supplemented with 10% FBS, Glutamax I and Gentamicin. When the cells were 60-70% confluent, they were transfected in duplicates with different concentrations of oligonucleotides (0.04-25 nM) using Lipofectamine 2000 (5 µg/mL and 10 µg/ml for Huh-7 and Hepa 1-6, respectively). Transfections were carried out essentially as described by Dean et al. (1994, JBC 269:16416-16424). In short, cells were preincubated for 7 min. with Lipofectamine in Opti-MEM followed by addition of oligonucleotide to a total volume of 1.5 mL transfection mix per well. After 4 hours, the transfection mix was removed; cells were washed and grown at 37° C. for approximately 20 hours (mRNA analysis and protein analysis) in the appropriate growth medium. Cells were then harvested for protein and RNA analysis.

Example 6

In Vitro Model: Extraction of RNA and cDNA Synthesis

Total RNA Isolation

Total RNA was isolated using RNeasy mini kit (Qiagen). Cells were washed with PBS, and Cell Lysis Buffer (RTL, Qiagen) supplemented with 1% mercaptoethanol was added directly to the wells. After a few minutes, the samples were processed according to manufacturer's instructions.

First Strand Synthesis

First strand synthesis was performed using either OmniScript Reverse Transcriptase kit or M-MLV Reverse transcriptase (essentially as described by manufacturer (Ambion)) according to the manufacturer's instructions (Qiagen). When using OmniScript Reverse Transcriptase 0.5 µg total RNA each sample, was adjusted to 12 µl and mixed with 0.2 µl poly (dT)$_{12-18}$ (0.5 µg/µl) (Life Technologies), 2 µl dNTP mix (5 mM each), 2 µl 10×RT buffer, 0.5 µl RNAguard™ RNase Inhibitor (33 units/mL, Amersham) and 1 µl OmniScript Reverse Transcriptase followed by incubation at 37° C. for 60 min. and heat inactivation at 93° C. for 5 min.

When first strand synthesis was performed using random decamers and M-MLV-Reverse Transcriptase (essentially as described by manufacturer (Ambion)) 0.25 µg total RNA of each sample was adjusted to 10.8 µl in $H_2O$. 2 µl decamers and 2 µl dNTP mix (2.5 mM each) was added. Samples were heated to 70° C. for 3 min. and cooled immediately in ice water and added 3.25 µl of a mix containing (2 µl 10×RT buffer; 1 µl M-MLV Reverse Transcriptase; 0.25 µl RNAase inhibitor). cDNA is synthesized at 42° C. for 60 min followed by heating inactivation step at 95° C. for 10 min and finally cooled to 4° C.

Example 7

Results of Screening Different LNA Oligonucleotides apoB mRNA expression was determined by real-time quantitative PCR in Huh-7 cells after treatment with compounds SEQ ID NOs 26-50. Data are normalized to GAPDH and normalized to the mock control (FIGS. 1A and B).

Example 8

Cholesterol Levels in Serum

Total cholesterol level is measured in plasma using a colormetric assay Cholesterol CP from ABX Pentra. The cholesterol is measured following enzymatic hydrolysis and oxidation. 21.5 µL water was added to 3 µL serum. 250 µL reagent is added and within 15 min the cholesterol content is measured at a wavelength of 540 nM. Measurements on each animal were made in duplicates. The sensitivity and linearity was tested with dilution series of a control compound (ABX Pentra N control). The cholesterol level was determined by subtraction of the background and presented relative to the cholesterol levels in serum of saline treated mice.

In Vivo Studies

The LNA oligonucleotides were in the below present studies administered to C57BL/6J female mice on a standard chow diet.

Example 9

Results of Screening Different LNA Oligonucleotides In Vivo

In this study mice were administered the LNA oligonucleotides subcutaneously once weekly for 4 weeks (total of 5 administrations) at two different dose levels (10 mg/kg of SEQ ID NO 28, 29, 44 and 45). Serum was sampled once weekly and at sacrifice (48 hours after last administration) to examine the effect of the compounds on total cholesterol.

Figure 2:
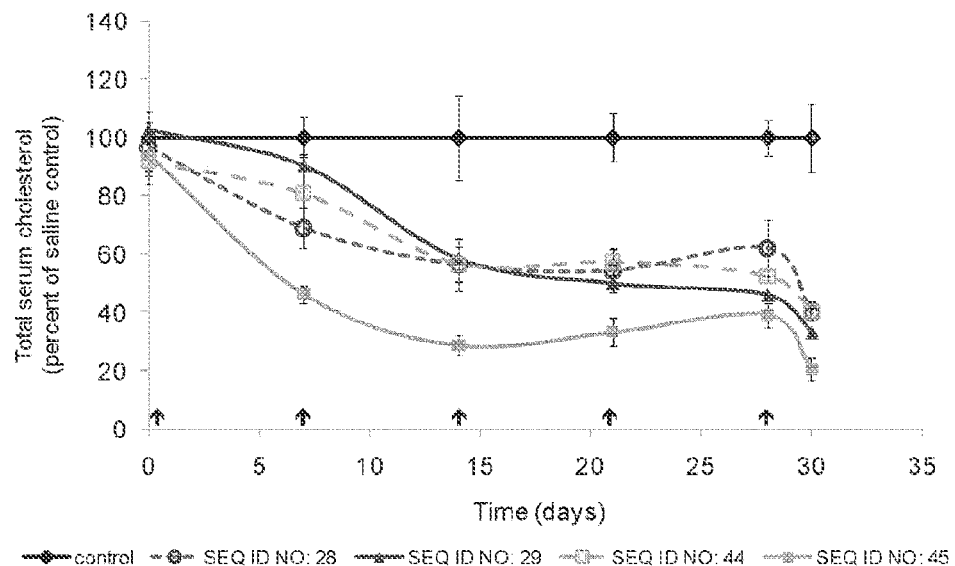
FIG. 2: Total serum cholesterol measured once weekly in C57BL/6J mice administered 10 mg/kg SEQ ID NOs: 28, 29, 44 or 45 for 4 weeks and at sacrifice 48 hours after last administration of LNA oligonucleotide. Data are presented relative to the control (administered saline) as mean±std, n=5. TC=total cholesterol.

Administration of any of the 4 LNA oligonucleotides resulted in a significant reduction in total cholesterol within the first week after administration. After 2 weeks a steady state in total cholesterol was obtained when measured one week after administration (40-65% reduction in total cholesterol). However, measuring total cholesterol 48 hours after administration showed further reduction in total cholesterol as observed at sacrifice day 30 with 60-80% reduction in total cholesterol, indicating maximum effect on total cholesterol 2-3 days after administration (FIG. 2).

Example 10

Results of Repeated Dosing of Different LNA Oligonucleotides In Vivo

In this study mice were administered the LNA oligonucleotides subcutaneously once weekly for 4 weeks (total of 5 administrations). SEQ ID NO: 45 was dosed at 4 different dose levels (0.02, 0.4, 2 and 10 mg/kg/week), whereas SEQ ID NOs: 29 and 51 were dosed at 10 mg/kg/week. Serum was sampled once weekly and at sacrifice (48 hours after last administration) to examine the effect of the compounds on total cholesterol.

Figure 3A:
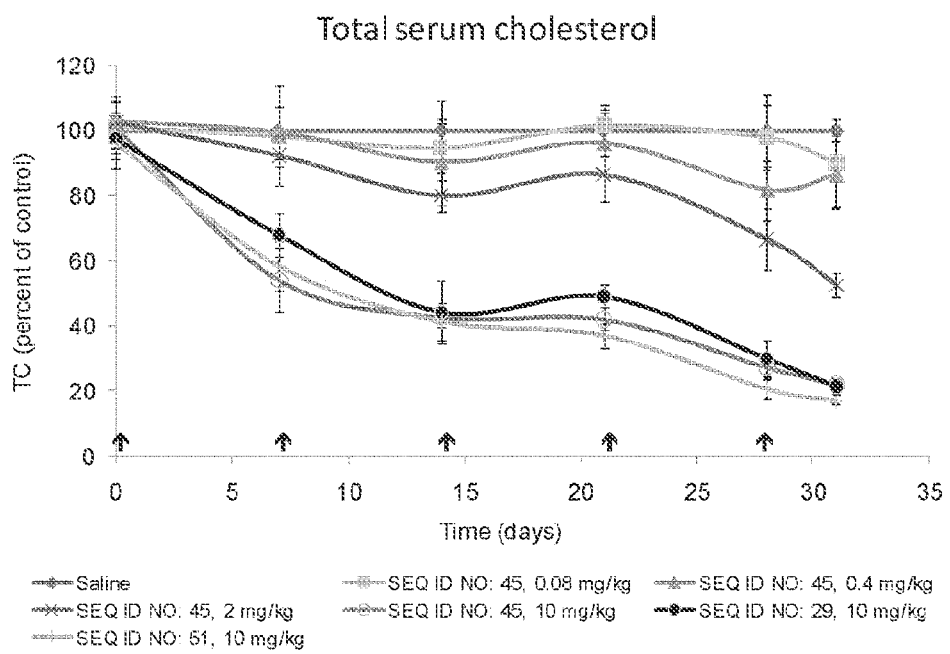
FIG. 3: Repeated dosing of 3 different oligonucleotides targeting apoB, SEQ ID NO: 45 at different dose levels. The figure shows the A) effect on total cholesterol measured in serum one week after dosing and B) ALT levels at the end of the study.
Figure 3B:
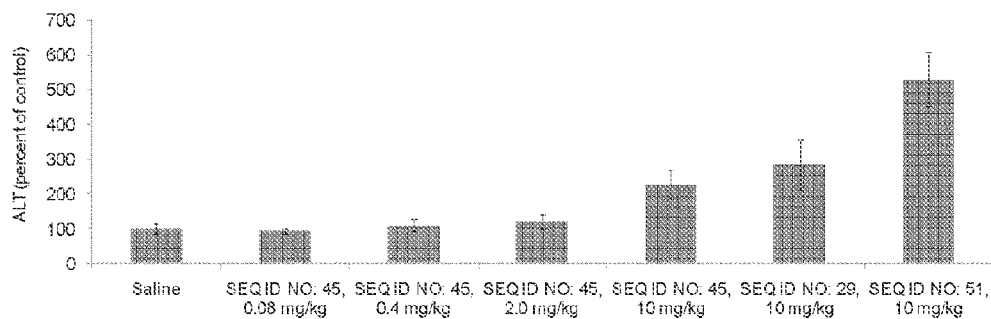

Administration of any of the 3 LNA oligonucleotides at 10 mg/kg/week resulted in a significant reduction in total cholesterol within the first week after administration. After 2 and 4 weeks, respectively, when measured one week after administration, reduction in total cholesterol of 58 and 70% was obtained with all three compounds (FIG. 3A). Analysis of the ALT levels in serum showed increases at the 10 mg/kg/week dose levels, but for SEQ ID NOs: 29 and 45 this was within the normal range, whereas SEQ ID NO: 51 resulted in 5 fold increase in serum ALT level (FIG. 3B).

Example 11

Duration of Action of a Single Dose of SEQ ID NO: 29

Figure 4A:
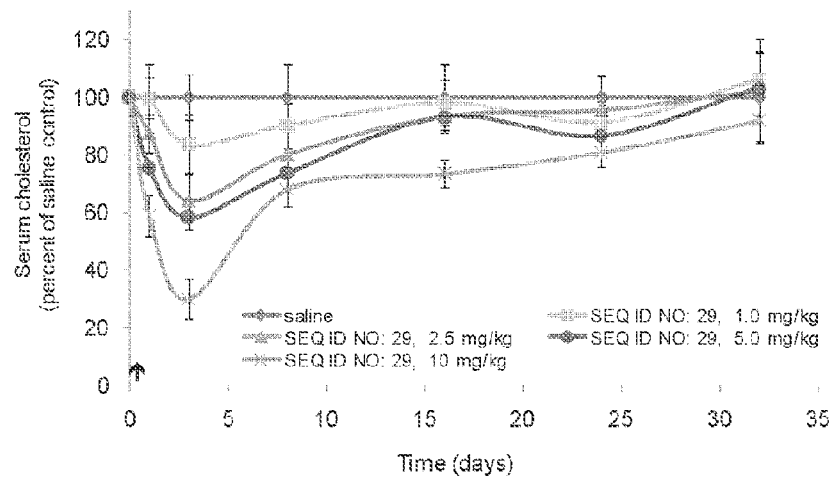
FIG. 4: Total serum cholesterol levels (A) and effect on HDL/LDL ratio (B) at different time point after a single administration of SEQ ID NO: 29 at different dose levels.

Mice were administered one intravenous dose of SEQ ID NO: 29 on day 0 at different dose levels (1, 2.5, 5 and 10 mg/kg), and serum cholesterol was measured at days 0, 1, 3, 8, 16, 24 and 32. Already one day after administration of the oligonucleotide significant effect was obtained on total cholesterol at 5 and 10 mg/kg. Maximum effect on cholesterol, was measured at day 3; 16%, 36%, 42% and 70% reduction in total serum cholesterol for 1, 2.5, 5 and 10 mg/kg, respectively. After 24 days the total cholesterol levels were still significantly reduced by 13% and 19% in the 5 and 10 mg/kg dose levels groups (FIG. 4A).

Figure 4B:
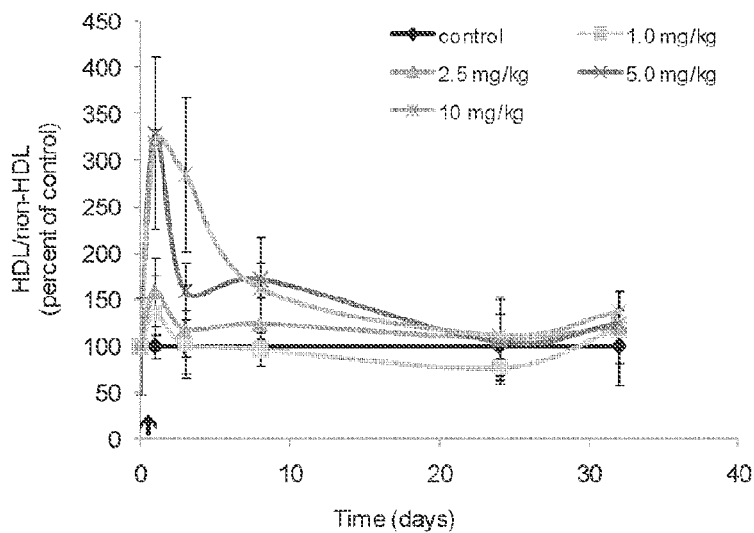

The fast lowering effect on apoB was demonstrated on the lipoprotein profile. The HDL/non-HDL ratio increased very fast after administration of the oligonucleotide. The ratio increased in a dose dependent manner 140-170% at the low dose levels (1 and 2.5 mg/kg) and 325% at the high dose levels (5 and 10 mg/kg) already 24 hours after dosing (FIG. 4B).

Example 12

Repeated Dosing Once Weekly or Biweekly of SEQ ID NO: 29

Figure 5A:
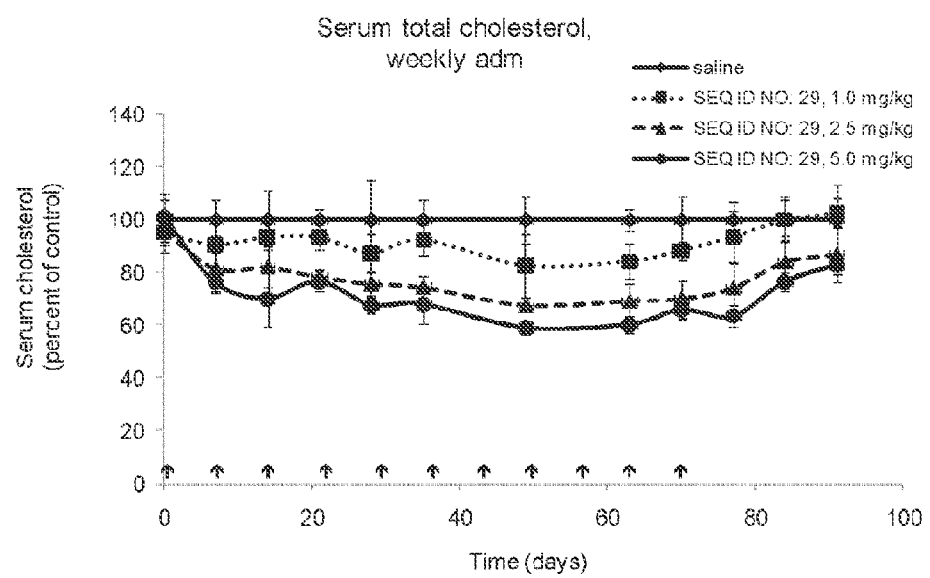
FIG. 5: Total serum cholesterol measured weekly one week after dosing (arrows indicate dosing A) once weekly, B) once biweekly). Mice were dosed for 70 days and recovered 1 to 3 weeks after last dose before sacrifice.
Figure 5B:
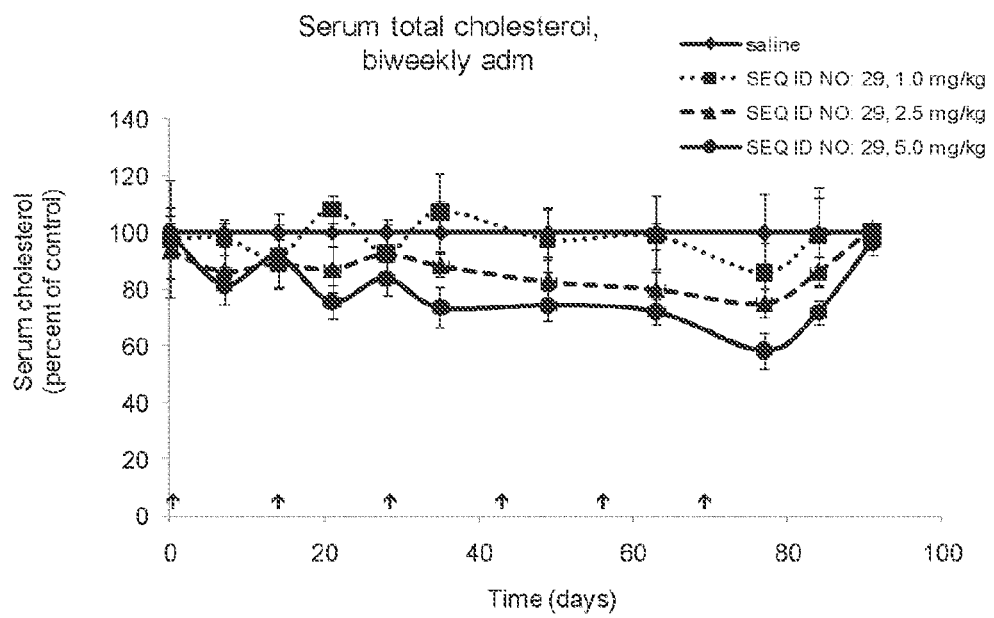

Mice were subcutaneously administered SEQ ID NO: 29 at dose levels 1, 2.5 or 5 mg/kg once weekly or once biweekly for 70 days. Following the treatment period mice recovered 7 or 21 days before sacrifice. Serum was sampled once weekly during the first 5 weeks, followed by biweekly sampling from day 35 to day 63 and weekly sampling again from day 63 to day 91. In the groups dosed weekly, at day 14 (after 2 doses) total serum cholesterol reached sustained levels of reduction of approximately 30-40% for the 2.5 and 5 mg/kg dose levels, whereas the 1 mg/kg dose levels gave mean sustained effect of only 10% reduction in total cholesterol during the treatment period (FIG. 5A). Decreasing the frequency of dosing to biweekly dosing, sustained reduction in total cholesterol was obtained later from day 35, at 30% and 20% for the 2.5 and 5 mg/kg dose levels. One mg/kg dose level did not give any reduction in total cholesterol (FIG. 5B).

During the recovery period the effect decreased and in the groups dosed biweekly cholesterol had returned to base line at day 91 for all dose levels. In the groups dosed weekly the 2.5 and 5 mg/kg groups still had 13-17% reduction in serum total cholesterol at the end of the recovery period.

Figure 6:
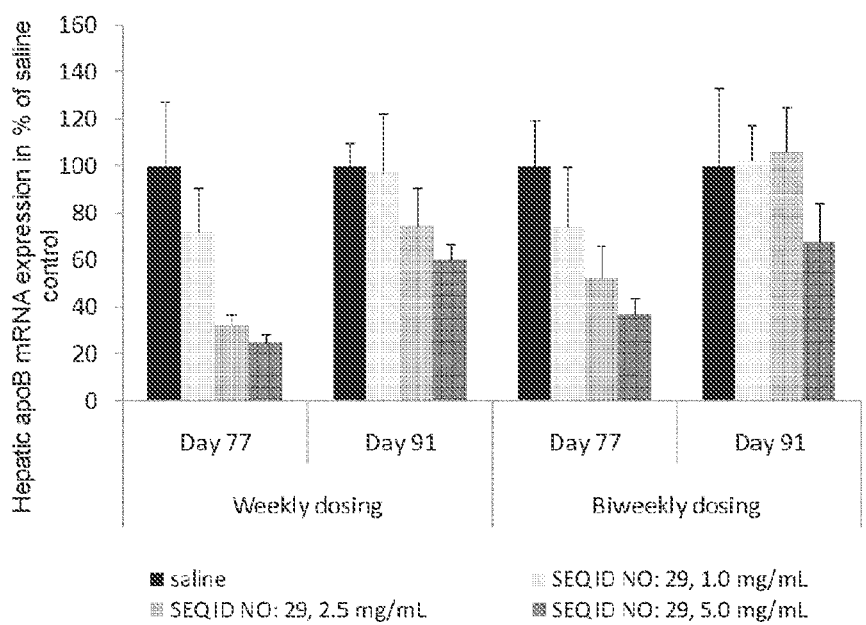
FIG. 6: ApoB mRNA expression in liver at day 77 (end of treatment, 7 days after last dose) and day 91 (end of recovery period)

One and three weeks after the end of treatment mice were sacrificed, livers were sampled for qPCR analysis to determine the expression of hepatic apoB mRNA. Both weekly and biweekly dosing resulted in a dose dependent down regulation of apoB mRNA expression (FIG. 6). Weekly dosing of 5 mg/kg gave the highest effect, 75% reduction in apoB mRNA, whereas biweekly dosing gave 63% reduction. After 3 weeks of recovery only the 2.5 and 5 mg/kg/week groups and the 5 mg/kg/biweekly had measurable reductions in hepatic apoB levels compared to the control; 25%, 40% and 33% respectively.

Figure 7:
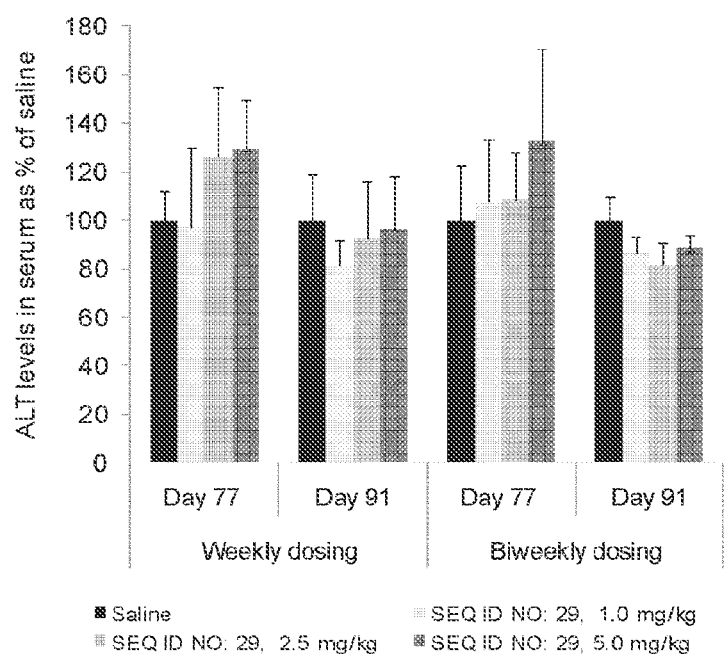
FIG. 7: ALT levels in serum at sacrifice day 77, one week after last dosing and day 91, 3 weeks after last dosing.

Serum ALT levels were measured days 77 and 91. No significant differences compared to the saline control were observed in ALT, neither at day 77 nor at day 91 (FIG. 7).

The invention claimed is:

1. A single stranded oligomer of 12-18 nucleotides comprising a contiguous nucleotide sequence that is at least 90% identical SEQ ID NO:4 wherein the oligomer has six contiguous DNA nucleobases and at least two locked nucleic acids (LNA).

2. The single stranded oligomer of claim 1 wherein the contiguous nucleotide sequence is identical to SEQ ID NO:4.

3. The single stranded oligomer of claim 1 having 12-16 nucleotides.

4. The single stranded oligomer of claim 1 comprising one or more phosphothioate internucleotide linkages.

5. The single stranded oligomer of claim 1 wherein at least one of the LNA is an oxy-LNA.

6. The single stranded oligomer of claim 5 wherein at least one of the LNA is a methyl C-LNA.

7. The single stranded oligomer of claim 1 comprising SEQ ID NO:28 or SEQ ID NO:29.

8. A pharmaceutical composition comprising the single stranded oligomer of claim 1.

9. A method of treating a disorder selected from: example, different types of HDL/LDL cholesterol imbalance, dyslipidemia, acquired hyperlipidemia, hypercholesterolemia, statin-resistant hypercholesterolemia, coronary artery disease (CAD), coronary heart disease (CHD) and atherosclerosis, the method comprising administering to a patient and the single stranded oligomer of claim 1.

10. The single stranded oligomer of claim 1 having the formula

A-B-C, wherein:
A comprises 1-4 LNA nucleotides:
B comprises 6-12 consecutive DNA nucleotides; and
C comprises 1-4 LNA nucleotides.

11. The single stranded oligomer of claim 10 having 12-16 nucleotides.

12. The single stranded oligomer of claim 10, wherein:
A consists of 2 or 3 LNA nucleotides;
B consists of 8-10 consecutive DNA nucleotides; and
C consists of 2 or 3 LNA nucleotides.

13. The singled stranded oligomer of claim 1 having 12 nucleotides.

14. The single stranded oligomer of claim 10, wherein:
A consists of 2 LNA nucleotides;
B consists of 8 contiguous DNA nucleotides; and
C consists of 2 LNA nucleotides.

15. The single stranded oligomer of claim 1 having the formula $$5'\text{-}G_s T_s t_s g_s a_s c_s a_s c_s t_s g_s T_s{}^m C\text{-}3' \quad (\text{SEQ ID NO:29})$$

wherein capital letters represent LNA nucleobases, lower case letters represent DNA nucleotides, subscript s represent a phosphorothioate internucleoside linkage, and superscript m preceding a capital C indicates a 5-methyl cytosine LNA.

16. A pharmaceutical composition comprising the single stranded oligomer of claim 5 and a pharmaceutically acceptable carrier.

17. A pharmaceutical composition comprising the single stranded oligomer of claim 15 and a pharmaceutically acceptable carrier.

18. The single stranded oligomer of claim 2, wherein all internucleotide linkages are phosphothioate internucleotide linkages.

* * * * *